(12) United States Patent
Hughes

(10) Patent No.: US 11,925,254 B2
(45) Date of Patent: Mar. 12, 2024

(54) ARTICLE SHIELD APPARATUS

(71) Applicant: Harold M. Hughes, Aurora, CO (US)

(72) Inventor: Harold M. Hughes, Aurora, CO (US)

( * ) Notice: Subject to any disclaimer, the term of this patent is extended or adjusted under 35 U.S.C. 154(b) by 157 days.

(21) Appl. No.: 17/676,038

(22) Filed: Feb. 18, 2022

(65) Prior Publication Data

US 2022/0167731 A1  Jun. 2, 2022

Related U.S. Application Data

(63) Continuation-in-part of application No. 29/817,714, filed on Dec. 3, 2021, now abandoned, which is a continuation-in-part of application No. 29/748,274, filed on Aug. 28, 2020, now abandoned.

(51) Int. Cl.
*A45F 5/00* (2006.01)
*A61N 1/16* (2006.01)

(52) U.S. Cl.
CPC .............. *A45F 5/00* (2013.01); *A61N 1/16* (2013.01); *A45F 2005/002* (2013.01); *A45F 2005/008* (2013.01)

(58) Field of Classification Search
CPC .......... A45F 2005/008; A45F 2005/002; A45F 2200/0516; A45C 11/00; A45C 11/002; A45C 11/22; A45C 13/008; H04B 1/3888; B65D 33/00
USPC ................................................ 224/219, 222
See application file for complete search history.

(56) References Cited

U.S. PATENT DOCUMENTS

| | | | | |
|---|---|---|---|---|
| 2,107,216 | A * | 2/1938 | Rogers | A44B 19/32 206/274 |
| 4,637,063 | A * | 1/1987 | Sullivan | B65D 33/25 383/61.3 |
| 5,881,883 | A * | 3/1999 | Siegelman | B65D 81/03 206/720 |
| 8,137,618 | B2 * | 3/2012 | Zocchi | A61M 5/003 422/409 |
| 9,460,309 | B2 * | 10/2016 | Zar | B65D 33/00 |
| 2005/0263556 | A1 * | 12/2005 | Labit | A61F 15/001 190/102 |
| 2007/0215663 | A1 * | 9/2007 | Chongson | A45C 13/30 224/236 |
| 2013/0118935 | A1 * | 5/2013 | Zar | B65D 85/00 206/320 |
| 2014/0231277 | A1 * | 8/2014 | Ponski | A45C 11/00 206/38 |
| 2018/0140063 | A1 * | 5/2018 | Gomez | A45F 5/021 |
| 2018/0228260 | A1 * | 8/2018 | Cole | A45C 11/00 |
| 2021/0113880 | A1 * | 4/2021 | Bassoo | A63B 21/065 |

* cited by examiner

*Primary Examiner* — Adam J Waggenspack
(74) *Attorney, Agent, or Firm* — Roger A. Jackson

(57) ABSTRACT

An article shield apparatus adapted to protectively encompass an article, the apparatus including a first flexible surrounding sidewall that acts as a protective cover, a second flexible surrounding sidewall that is nested within the first flexible surrounding sidewall, the second surrounding sidewall functions as a radio frequency shield, in addition, a third flexible surrounding sidewall that is nested within the second surrounding sidewall with the third surrounding sidewall being constructed with from a waterproof material, wherein the third surrounding sidewall holds the article thus resulting in operationally the article being substantially protected from water and radio frequency waves.

9 Claims, 20 Drawing Sheets

ARTICLE SHIELD APPARATUS

RELATED APPLICATIONS

This application is a continuation in part of United States design patent application Ser. No. 29/817,714 filed on Dec. 3, 2021 by Harold M. Hughes of Aurora, Colorado, U.S., that is a continuation in part of United States design patent application Ser. No. 29/748,274 filed on Aug. 28, 2020 by Harold M. Hughes of Aurora, Colorado, U.S.

FIELD OF THE INVENTION

The present invention generally relates to a wearable apparatus that provides a specific benefit to the user, and more particularly to a wearable that is flexibly removably engageable to a user's wrist, wherein the wearable apparatus can hold an article in the form of a card, identification, and the like to protect the article from water and radio frequency waves plus have structure to make removing and adding the article from the wearable apparatus easy and convenient.

BACKGROUND OF THE INVENTION

In today's digital environment, an individual's personal items such as credit cards, debit cards, key fobs, and various other electronic devices transmit and receive radio signals on a regular basis wherein there is an ever present risk of the capture of these radio signals by nefarious third parties, wherein these radio signals contain multitudes of personal information being financial, medical, and so on, so this results in great interest in helping to thwart these nefarious third parties in capturing these radio signals. With this the use of the Faraday Cage is utilized to encompass the article with an electrically conductive material that effectively blocks the radio signals, while this seems easy enough, i.e. wrap the article in aluminum foil for instance, however this is not practical for everyday use to keep wrapping and unwrapping the article in aluminum, so electrically conductive flexible fabric was developed which allowed flexibility to make a pocket while retaining the needed electrical conductivity. However, this only partially solved the problem via getting rid of aluminum foil, as with any piece of fabric there has to be an opening in the electrically conductive fabric pocket to dispose into and remove the article from the electrically conductive fabric pocket. So, it is this opening that can be difficult to seal from radio frequency waves, and as a rule of thumb, any gaps or openings in the electrically conductive fabric need to be less than one-tenth of the wavelength of the radio frequency wave to block that radio wave, thus making the needed closure of any gaps or openings must be controlled and to be safe resulting in the gaps or openings needing to be minimized. So, this leads to the next problem, as a typical "seal" as between surfaces utilizes an elastomeric material in nature to accommodate the un-evenness as between the surfaces in other applications, however, for the Faraday Cage, this "seal" must be electrically conductive and also have elastomeric qualities, which can be a challenge to accomplish.

In looking at the prior art in this area in U.S. Pat. No. 5,083,111 to Drucker, discloses a signal jamming apparatus that creates a jamming zone for retail RFID tags and a non-jamming zone for RFID tags, wherein the jamming zone is facilitated by generation of a jamming signal, so this is an active system, compared to the Faraday Cage type that is passive via blocking or shielding outside signals. Further in the prior art in U.S. Pat. No. 7,221,900 to Reade discloses a jamming device against RFID smart tag systems that uses multiple RFID chips to confuse the RFID scanner.

Continuing in the prior art in U.S. Pat. No. 7,635,089 to Augustinowicz, discloses a device for shielding the reading of a contactless smartcard, a shielding material on a second panel that is hinged to a first panel, wherein the smartcard is sandwiched between the first and second panels such that when the panels are closed the smartcard cannot be read and when the panels are open the smartcard can be read. Augustinowicz is a sandwich RFID shield construction that has a closed state to block RFID signals and an open state to allow RFID signals.

Further in the prior art in U.S. Pat. No. 7,701,408 to Bombay, that discloses a shielded contactless electronic element, this is a lot like Augustinowicz in basic concept with the flat document and a hinged cover that while closed blocks RFID signals and while open allows RFID signals, however, instead of a passive shield like Augustinowicz, Bombay uses an active RFID block that includes an RF microcontroller, an antenna, and with a calibrated wire grid with spacing restricted to signal blocking, it is this reason that Bombay was patentable over Augustinowicz. Next, in the associated prior art in U.S. Pat. No. 8,955,759 to Finn, discloses inlays for security documents that involves a permanent layer bonding with a chip, and ferrite material, basically an RFID enhanced document for an alternative approach to some of the technology used in various RFID systems.

Moving onward in the referenced prior art, in U.S. Pat. No. 10,178,815 to Vieyra, discloses protected wearables that can include an RFID shield with a strap for securing to a user's body, wherein Vieyra has a non-specific RFID type shield with the claiming relating to the structure of the shield containment, with a non-specific RFID type shield in a wearable, however, not having any waterproofing.

Further, in the related prior art in U.S. Pat. No. 10,238,016 to Frank, discloses an electromagnetic interference containment system for an electronic system, wherein this is a different application of a RFID shield to protect a flash memory, as this fits in with most the patents in this area, being various structural applications of RFID shielding.

Continuing in the related prior art in U.S. Pat. No. 10,572,790 to Home, discloses a RFID disruption device for data storage i.e. a credit card, utilizing a proactive signal disruptor (as opposed to a passive shield), the RFID disruptor having a current regulator and high speed switch to generate a disruptive signal, somewhat like Bombay.

Further, in the related prior art in U.S. Pat. No. 10,783,335 to Carey, discloses a data protected RFID device that uses a camera that in conjunction with an electronic tagging system to tag the RFID read source, and to be able to block the RFID read source, with the system requiring a power supply being a proactive RFID block. Also, in the associated prior art in U.S. Pat. No. 10,814,833 to Goetzinger discloses an anti-theft car license plate display with an optional faraday cage (RFID shield), see claim 5, for blocking signals in the valuable vault in the license plate frame.

Continuing in the related prior art in U.S. Pat. No. 10,956,689 to Colby, discloses a passport that has RFID shielding, wherein the RFID shielding is in the cover being similar to Augustinowicz and in U.S. Pat. No. 11,109,496 to Williams, discloses a phone and tablet case that has an independent GPS system in the case plus an option for a passive or active RFID device. Further, in the related prior art in United States Patent Application Publication Number US2021/0112935 to Tran, discloses a wallet shell with side rails that give RFID access to a card disposed within the wallet and in United States Patent Application Publication Number US2021/0212424 to Sawadogo discloses a smart wallet that has among other things a RFID shield.

What is needed is an easy to use wearable radio frequency shield that preferably includes waterproofing for an the article, such as credit cards, debit cards, key fobs, and various other electronic devices that is easy to open and close plus easy to place on an arm or wrist to conveniently carry. Desirable invention elements include a removably engageable wrist band with a sealed waterproof pocket disposed within an RFID shield all encased within a protective cover.

SUMMARY OF INVENTION

Broadly, the present invention is an article shield apparatus adapted to protectively encompass an article, the article shield apparatus including a first flexible surrounding sidewall that is about a longitudinal axis, the first flexible surrounding sidewall having a first primary end portion terminating in a first primary margin and an opposing first secondary end portion terminating in a first secondary margin with the longitudinal axis spanning therebetween. The first flexible surrounding sidewall further including a first inner surface and an opposing first outer surface, the first secondary margin being affixed to itself to form a first interior as defined by the first inner surface and the first primary margin and said first secondary margin, with the first primary margin defining a first aperture opening that has a first open state and a first closed state.

Further included in the article shield apparatus is a second flexible surrounding sidewall that is about a lengthwise axis, the second flexible surrounding sidewall having a second primary end portion terminating in a second primary margin and an opposing second secondary end portion terminating in a second secondary margin with the lengthwise axis spanning therebetween, the second flexible surrounding sidewall further including a second inner surface and an opposing second outer surface. The second secondary margin being affixed to itself to form a second interior as defined by the second inner surface and the second primary margin and the second secondary margin, with the second primary margin defining a second aperture opening. Wherein, the second primary margin has a first means for removable engagement, wherein the second aperture opening having a second open state and a second closed state, the second flexible surrounding sidewall is nested within the first interior resulting in the second outer surface being adjacent to the first inner surface and the second secondary margin being adjacent to said first secondary margin with the longitudinal and lengthwise axes being coincident to one another, with the second aperture opening overlaying the first aperture opening, wherein the second flexible surrounding sidewall is constructed of a radio frequency blocking material.

In addition, for the article shield apparatus a third flexible surrounding sidewall is included that is about a longwise axis, the third flexible surrounding sidewall having a third primary end portion terminating in a third primary margin and an opposing third secondary end portion terminating in a third secondary margin with the longwise axis spanning therebetween. The third flexible surrounding sidewall further including a third inner surface and an opposing third outer surface, the third secondary margin being affixed to itself in a water proof manner to form a third interior as defined by the third inner surface and the third primary margin and the third secondary margin. With the third primary margin defining a third aperture opening in a third open state, the third flexible surrounding sidewall is nested within the second interior resulting in the third outer surface being adjacent to the second inner surface and the third secondary margin being adjacent to the second secondary margin with the lengthwise and longwise axes being coincident to one another, with the third aperture opening overlaying the second aperture opening, wherein the third flexible surrounding sidewall is constructed of a waterproof material. Wherein the third primary margin further comprises a removably engageable waterproof seal such that the third primary margin seals unto itself to make the third interior waterproof from an external environment in a third closed state of the third aperture opening, wherein operationally the article is disposed within the third interior and is protected in a waterproof enclosure that includes radio frequency shielding with an outer cover in the form of the first flexible surrounding sidewall in the first, second, and third closed states.

These and other objects of the present invention will become more readily appreciated and understood from a consideration of the following detailed description of the exemplary embodiments of the present invention when taken together with the accompanying drawings, in which;

BRIEF DESCRIPTION OF DRAWINGS

FIG. 17 is cross section cut 17-17 from FIGS. 6 and 8, wherein FIG. 17 shows the first, second, and third flexible surrounding sidewalls all nested to one another, all in the first, second, and third open states, wherein the first flexible surrounding sidewall showing the fifth means for removable engagement in the form of a hook and loop fastener, the second flexible surrounding sidewall showing the sixth means for removable engagement in the form of the elastically conductive flexible seal, and the third flexible surrounding sidewall showing the first means for removable engagement in the form of a waterproof seal with male and interlocking female dovetail channels, all in the first, second, and third alternative open states;

FIG. 18 is cross section cut 18-18 from FIG. 2, wherein FIG. 18 shows the first, second, and third flexible surrounding sidewalls all nested to one another, all in the first, second, and third closed states, wherein the first flexible surrounding sidewall showing the fifth means for removable engagement in the form of a hook and loop fastener, the second flexible surrounding sidewall showing the sixth means for removable engagement in the form of the elastically conductive flexible seal, and the third flexible surrounding sidewall showing the first means for removable engagement in the form of a waterproof seal with male and interlocking female dovetail channels, all in the first, second, and third alternative closed states;

FIG. 19d is a side elevation end view of the perspective view of FIG. 19c, wherein FIG. 19d shows the second flexible surrounding sidewall with the fold over extension with the closed state of the second aperture with a second fold over utilizing the fourth means of removable engagement the form of a hook and loop fastener.

REFERENCE NUMBERS IN DRAWINGS

Figure 1:
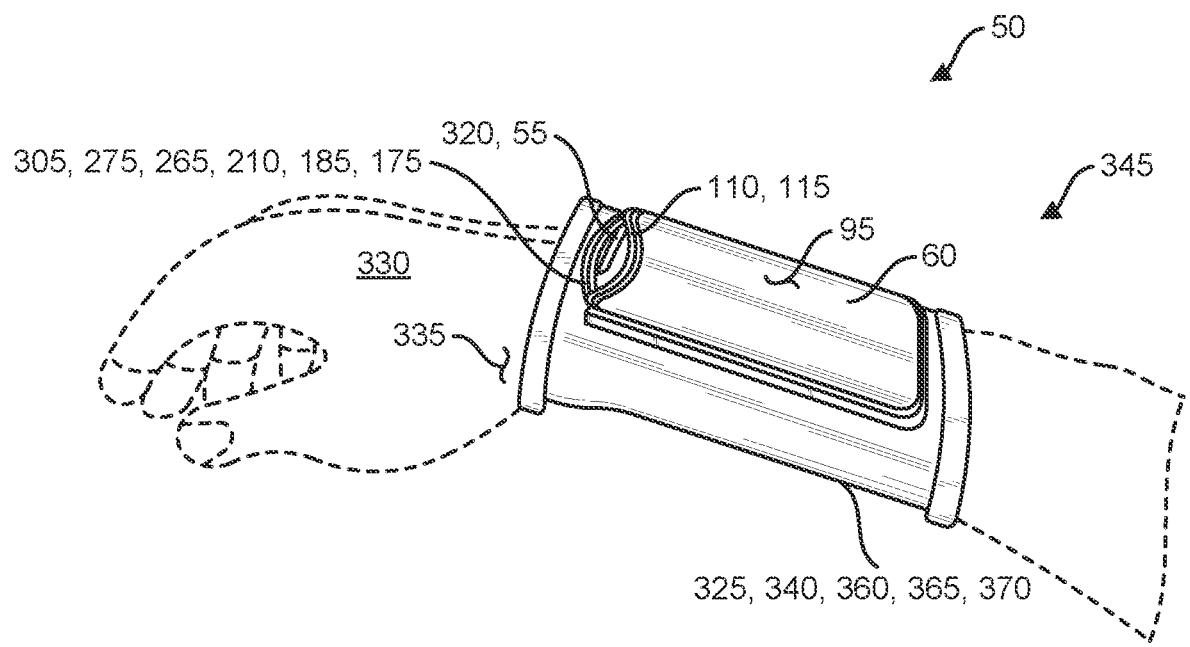
FIG. 1 shows an upper perspective view of the article shield apparatus that shows the article that is inserted in a first, second, and third aperture openings in their respective first, second and third open states, with the article shield apparatus disposed on the user's wrist via an elastomeric open ended tube shape holder.

50 Article shield apparatus
55 Article
60 First flexible surrounding sidewall
65 Longitudinal axis of the first flexible surrounding sidewall 60
70 First primary end portion of the first flexible surrounding sidewall 60
75 First primary margin of the first flexible surrounding sidewall 60
80 First secondary end portion of the first flexible surrounding sidewall 60
85 First secondary margin of the first flexible surrounding sidewall 60
90 First inner surface of the first flexible surrounding sidewall 60
95 First outer surface of the first flexible surrounding sidewall 60
100 Affixed nature of the first secondary margin 85 to itself
105 First interior of the first flexible surrounding sidewall 60
110 First aperture opening of the first flexible surrounding sidewall 60
115 First open state of the first flexible surrounding sidewall 60
120 First closed state of the first flexible surrounding sidewall 60
125 Second flexible surrounding sidewall
130 Lengthwise axis of the second flexible surrounding sidewall 125

135 Second primary end portion of the second flexible surrounding sidewall 125
140 Second primary margin of the second flexible surrounding sidewall 125
145 Second secondary end portion of the second flexible surrounding sidewall 125
150 Second secondary margin of the second flexible surrounding sidewall 125
155 Second inner surface of the second flexible surrounding sidewall 125
160 Second outer surface of the second flexible surrounding sidewall 125
165 Affixed nature of the second secondary margin 150 to itself
170 Second interior of the second flexible surrounding sidewall 125
175 Second aperture opening of the second flexible surrounding sidewall 125
180 First means for removable engagement of the second primary margin 140
185 Open state of the second aperture 175
190 Closed state of the second aperture 175
195 Nested nature of the second flexible surrounding sidewall 125 within the first interior 105
200 Adjacent nature of the second outer surface 160 to the first inner surface 90
205 Coincident nature of the longitudinal axis 65 and the lengthwise axis 130
210 Overlaying of the second aperture opening 175 relative to the first aperture opening 110
215 Third flexible surrounding sidewall
220 Longwise axis of the third flexible surrounding sidewall 215
225 Third primary end portion of the third flexible surrounding sidewall 215
230 Third primary margin of the third flexible surrounding sidewall 215
235 Third secondary end portion of the third flexible surrounding sidewall 215
240 Third secondary margin of the third flexible surrounding sidewall 215
245 Third inner surface of the third flexible surrounding sidewall 215
250 Third outer surface of the third flexible surrounding sidewall 215
255 Affixed nature of the third secondary margin 240 to itself
260 Third interior of the third flexible surrounding sidewall 215
265 Third aperture opening of the third flexible surrounding sidewall 215
270 First means for removable engagement of the third primary margin 230, plus alternatively the third axial margin 515, and the third secondary margin 240
275 Third open state of the third aperture opening 265
280 Third closed state of the third aperture 265
285 Nested nature of the third flexible surrounding sidewall 215 within the second interior 170
290 Adjacent nature of the third outer surface 250 to the second inner surface 155
295 Adjacent nature of the third secondary margin 240 to the second secondary margin 150
300 Coincident nature of the longwise axis 220 and the lengthwise axis 130
305 Underlaying of the second aperture opening 175 relative to the third aperture opening 265

310 Removably engageable waterproof seal of the third primary margin 230
315 External environment
320 Disposed nature of the article 55 in the third interior 260
325 Second means for removable attachment that is disposed on a portion of the first outer surface 95
330 Body part
335 Wrist
340 Adapted to attach to the body part 330 by the second means 325
345 Wearable
350 Strap of the second means 325
355 Hook and loop fastener of the strap 350 of the second means 325
360 Adapted to removably engage the wrist 335 by the strap 350 of the second means 325
365 Elastomeric open ended tube shape of the second means 325
370 Adapted to removably engage the wrist 335 by the elastomeric open ended tube shape 365
375 Pocket disposed between the first 60 and second 125 flexible surrounding sidewalls
380 Slot of the pocket 375
385 Manual open and close of the pocket slot 380
390 Third means for removable engagement for the pocket slot 380
395 Zipper of the third means 390
400 Fold over extension of the second flexible surrounding sidewall 125 second primary margin 140
405 At least two-fold overs of the fold over extension 400
410 Tortuous path of the two-fold overs 405 to help block radio frequency signals
415 Fourth means for removable engaging the at least two-fold overs 405
420 Hook and loop fastener of the fourth means 415
425 First axial margin of the first flexible surrounding sidewall 60
430 Parallel position of the first axial margin 425 to the longitudinal axis 65
435 First alternative open state
440 First alternative closed state
445 Fifth means for removable engagement to facilitate attachment in a first alternative closed state 440 and removal in a first alternative open state 435 of the first primary margin 75 to itself, the first axial margin 425 to itself, and the first secondary margin 85 to itself
450 First alternative interior as defined by the first inner surface 90, the first primary margin 75, the first axial margin 425, and the first secondary margin 85 all being in the first alternative closed state 440
455 First opening formed for the first flexible surrounding sidewall 60 in the first alternative open state 435
460 Second axial margin of the second flexible surrounding sidewall 125
465 Parallel position of the second axial margin 460 to the lengthwise axis 130
470 Second alternative open state
475 Second alternative closed state
480 Sixth means for removable engagement to facilitate attachment in a second alternative closed state 475 and removal in a second alternative open state 470 of the second primary margin 140 to itself, the second axial margin 460 to itself, and the second secondary margin 150 to itself
485 Second alternative interior as defined by the second inner surface 155, the second primary margin 140, the second axial margin 460, and the second secondary margin 150 all being in the second alternative closed state 475
490 Second opening formed for the second flexible surrounding sidewall 125 in the second alternative open state 470
495 Nesting of the second flexible surrounding sidewall 125 in the first alternative interior 450
500 Adjacent position of the second outer surface 160 to the first inner surface 90
505 Adjacent position of the first axial margin 425 to the second axial margin 460
510 Underlaying of the second opening 490 relative to the first opening 455
515 Third axial margin of the second flexible surrounding sidewall 125
520 Parallel position of the third axial margin 515 to the longwise axis 220
525 Removably engageable waterproof seal of the third primary margin 230 to itself, the third axial margin 515 to itself, and the third secondary margin 240 to itself to facilitate the third alternative open 530 and closed 535 states
530 Third alternative open state
535 Third alternative closed state
540 Third alternative interior as defined by the third inner surface 245, the third primary margin 230, the third axial margin 515, and the third secondary margin 240 all being in the third alternative closed state 535
545 Third opening formed for the third flexible surrounding sidewall 215 in the third alternative open state 530
550 Nesting of the third flexible surrounding sidewall 215 in the second alternative interior 485
555 Adjacent position of the third outer surface 250 to the second inner surface 155
560 Adjacent position of the second axial margin 460 to the third axial margin 515
565 Underlaying of the third opening 545 relative to the second opening 490
570 Seventh means for removable attachment that is disposed on a portion of the first outer surface
575 Adapted to attach to the body part 330 by the seventh means 570
580 Strap of the seventh means 570
585 Hook and loop fastener of the strap 580 of the seventh means 570
590 Adapted to removably engage the wrist 335 by the strap 580 of the seventh means 570
595 Elastomeric open ended tube shape of the seventh means 570
600 Adapted to removably engage the wrist 335 by the elastomeric open ended tube shape 595
605 Eighth means for removable engagement for the pocket slot 380
610 Zipper of the eighth means 605
615 Fifth means for removable engagement
620 Hook and loop fastener for the fifth means 615
625 Electrically conductive flexible seal that adhesively attaches to the second flexible surrounding sidewall 125 for the sixth means 480 for removable engagement
630 Elastomeric core
635 Electrically conductive flexible fabric that encases the elastomeric core 630
640 Outer surface of the electrically conductive flexible fabric 635
645 Inner surface of the electrically conductive flexible fabric 635
650 Substantial tube type shape of the outer surface 640
655 Lengthways axis of the tube type shape 650
660 First adhesive
665 Second adhesive
670 Parallel and opposite positions of the first 660 and second 665 adhesives about the lengthways axis 655
675 Flexible releasable interlocking and mating male 680 and female 685 channels
680 Male channel
685 Female channel
690 Dovetail type cross section of the male 680 and female 685 channels

DETAILED DESCRIPTION

Figure 2:
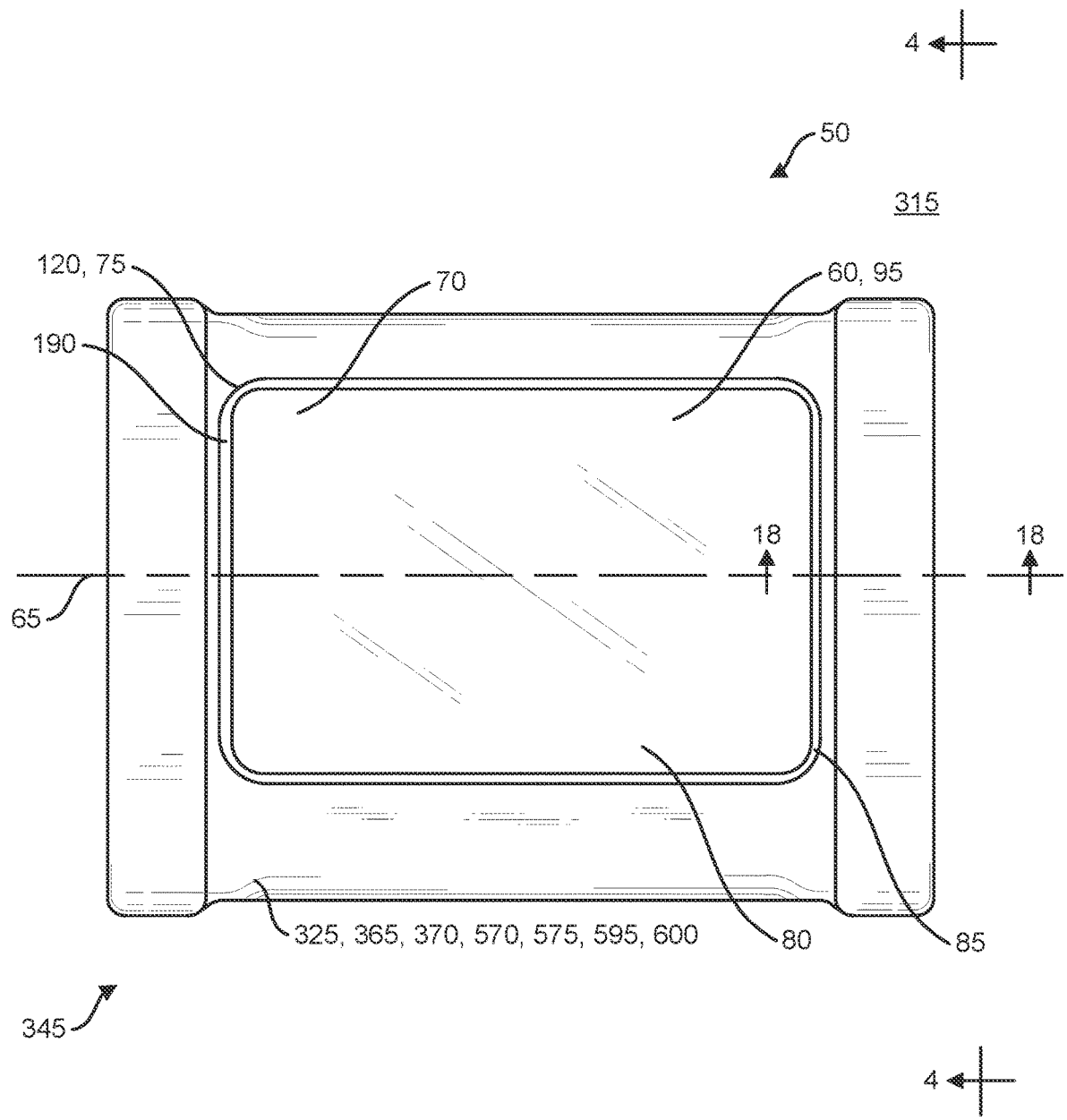
FIG. 2 shows a top view of the article shield apparatus that shows the first, second, and third aperture openings in their respective first, second and third closed states, with the elastomeric open ended tube shape holder.

With initial reference to FIG. 1 shown is an upper perspective view of the article shield apparatus 50 that shows the article 55 that is inserted in a first 110, second 175, and third 265 aperture openings in their respective first 115, second 185 and third 275 open states, with the article shield apparatus 50 disposed on the user's 330 wrist 335 via an elastomeric open ended tube shape holder 365. Next, FIG. 2 shows a top view of the article shield apparatus 50 that shows the first 110, second 175, and third 275 aperture openings in their respective first 120, second 190 and third 280 closed states, with the elastomeric open ended tube shape holder 365.

Figure 3:
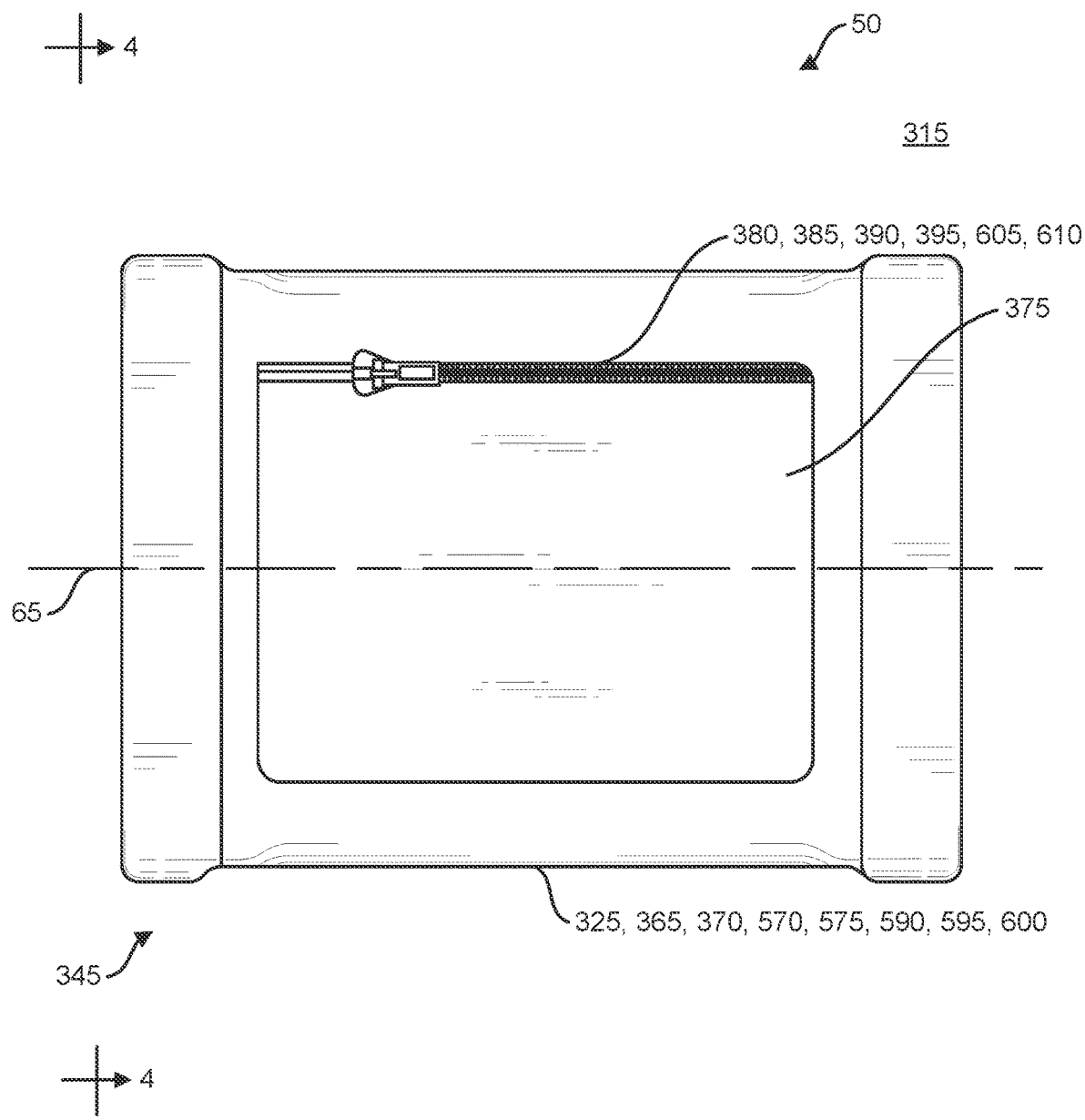
FIG. 3 shows a bottom view of the article shield apparatus that shows the pocket that is disposed between the first and second flexible surrounding sidewalls with a zipper for the third means of removable engagement for the pocket slot.

Continuing, FIG. 3 shows a bottom view of the article shield apparatus 50 that shows the pocket 375 that is disposed between the first 60 and second 125 flexible surrounding sidewalls with a zipper 395 for the third means 390 of removable engagement for the pocket slot 380.

Figure 4:
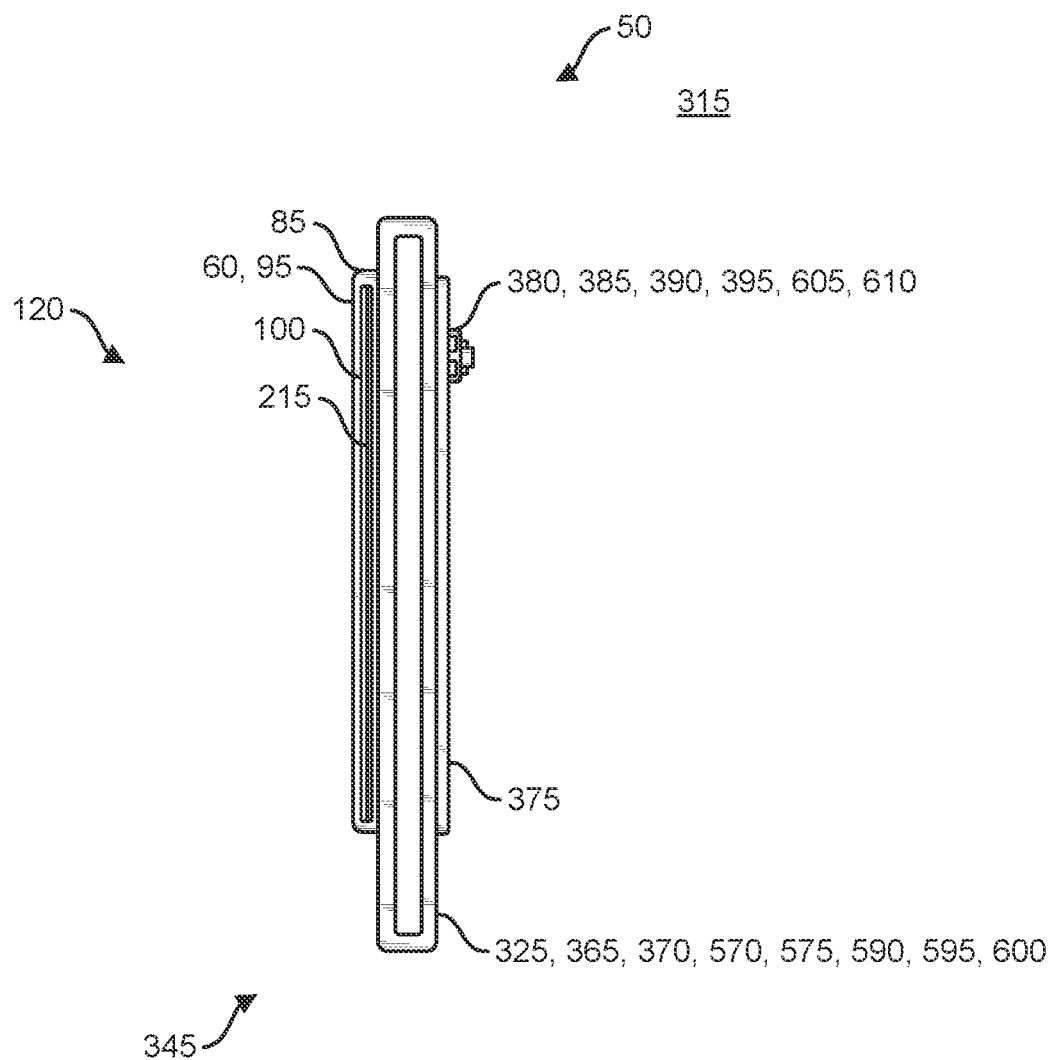
FIG. 4 shows a side elevation end view of the article shield apparatus that shows the first, second, and third flexible surrounding sidewalls in their respective first, second, and third closed states, with the elastomeric open ended tube shape holder, also shown is the bottom view of the article shield apparatus that shows the pocket that is disposed between the first and second flexible surrounding sidewalls with a zipper for the third means of removable engagement for the pocket slot.

Further, FIG. 4 shows a side elevation end view of the article shield apparatus 50 that shows the first 60, second 125, and third 215 flexible surrounding sidewalls in their respective first 120, second 190, and third 280 closed states, with the elastomeric open ended tube shape holder 365, also shown is the bottom view of the article shield apparatus 50 that shows the pocket 375 that is disposed between the first 60 and second 125 flexible surrounding sidewalls with the zipper 395 for the third means 390 of removable engagement for the pocket slot 380.

Figure 5:
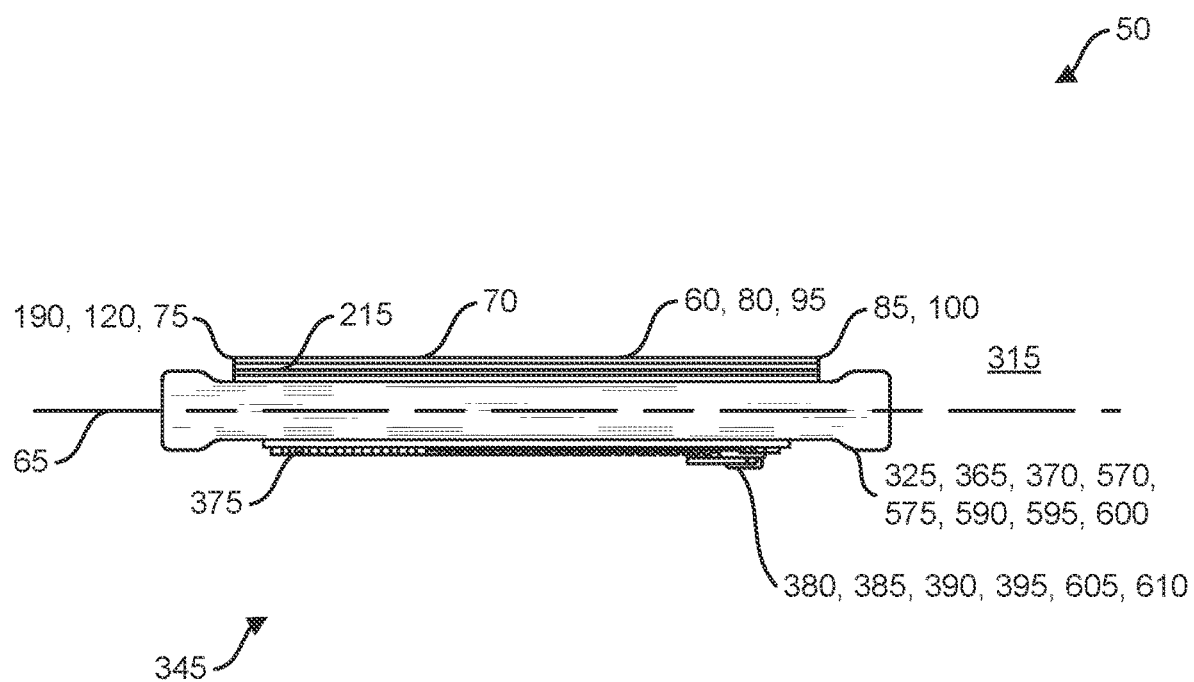
FIG. 5 shows a side elevation view of the article shield apparatus that shows the first, second, and third flexible surrounding sidewalls in their respective first, second, and third closed states, with the elastomeric open ended tube shape holder, also shown is the bottom view of the article shield apparatus that shows the pocket that is disposed between the first and second flexible surrounding sidewalls with a zipper for the third means of removable engagement for the pocket slot.

Next, FIG. 5 shows a side elevation view of the article shield apparatus 50 that shows the first 60, second 125, and third 215 flexible surrounding sidewalls in their respective first 120, second 190, and third 280 closed states, with the elastomeric open ended tube shape holder 365, also shown is the bottom view of the article shield apparatus 50 that shows the pocket 375 that is disposed between the first 60 and second 125 flexible surrounding sidewalls with the zipper 395 for the third means 390 of removable engagement for the pocket slot 390.

Figure 6:
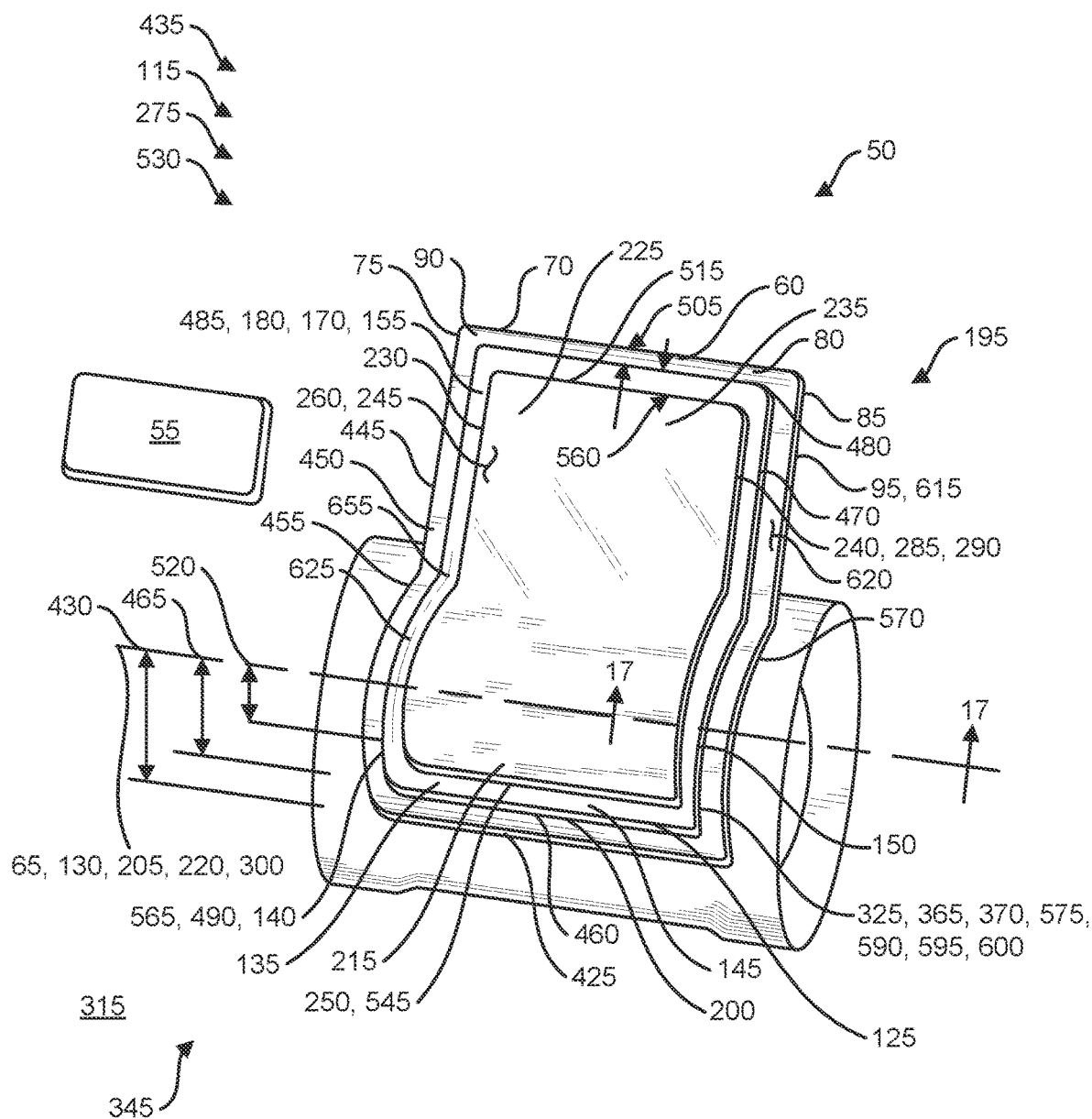
FIG. 6 shows an upper perspective view of the article shield apparatus that shows the article about to be inserted in a first, second, and third openings in their respective first, second and third alternative open states, with the elastomeric open ended tube shape holder.

Further, FIG. 6 shows an upper perspective view of the article shield apparatus 50 that shows the article 55 about to be inserted in a first 455, second 490, and third 545 openings in their respective first 435, second 470, and third 530 alternative open states, with the elastomeric open ended tube shape holder 365.

Figure 7:
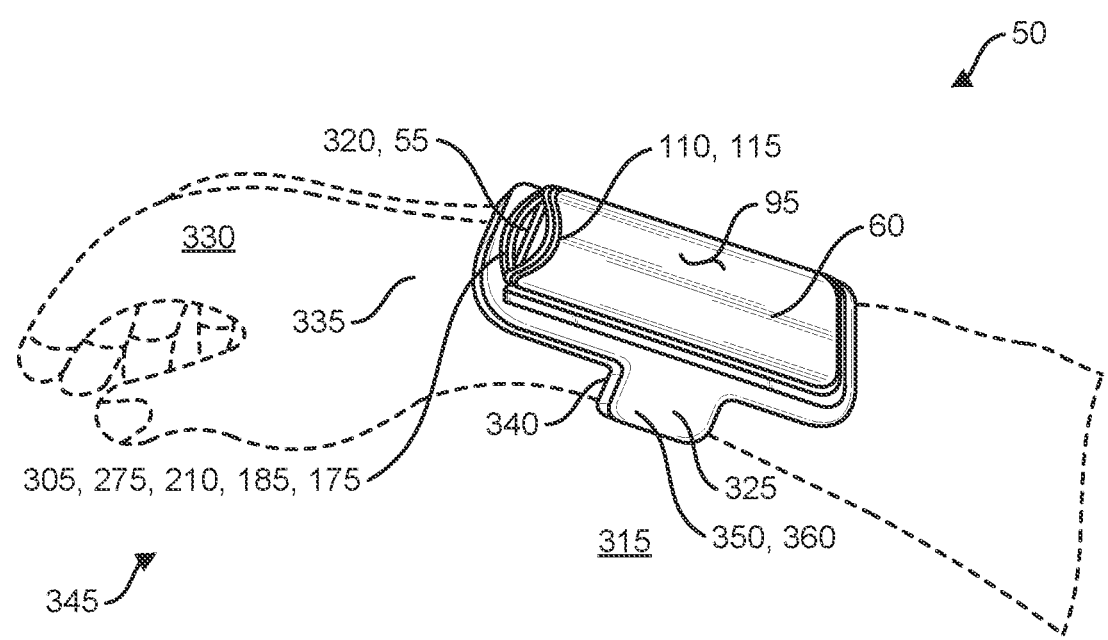
FIG. 7 shows an upper perspective view of the article shield apparatus that shows the article that is inserted in a first, second, and third aperture openings in their respective first, second, and third open states, with the article shield apparatus disposed on the user's wrist via a strap for the second means for removable attachment that is disposed on a portion of the first outer surface.

Next, FIG. 7 shows an upper perspective view of the article shield apparatus 50 that shows the article 55 that is inserted in the first 110, second 175, and third 265 aperture openings in their respective first 115, second 185, and third 275 open states, with the article shield apparatus 50 disposed on the user's 330 wrist 335 via a strap 350 for the second means 325 for removable attachment that is disposed on a portion of the first outer surface 95.

Figure 8:
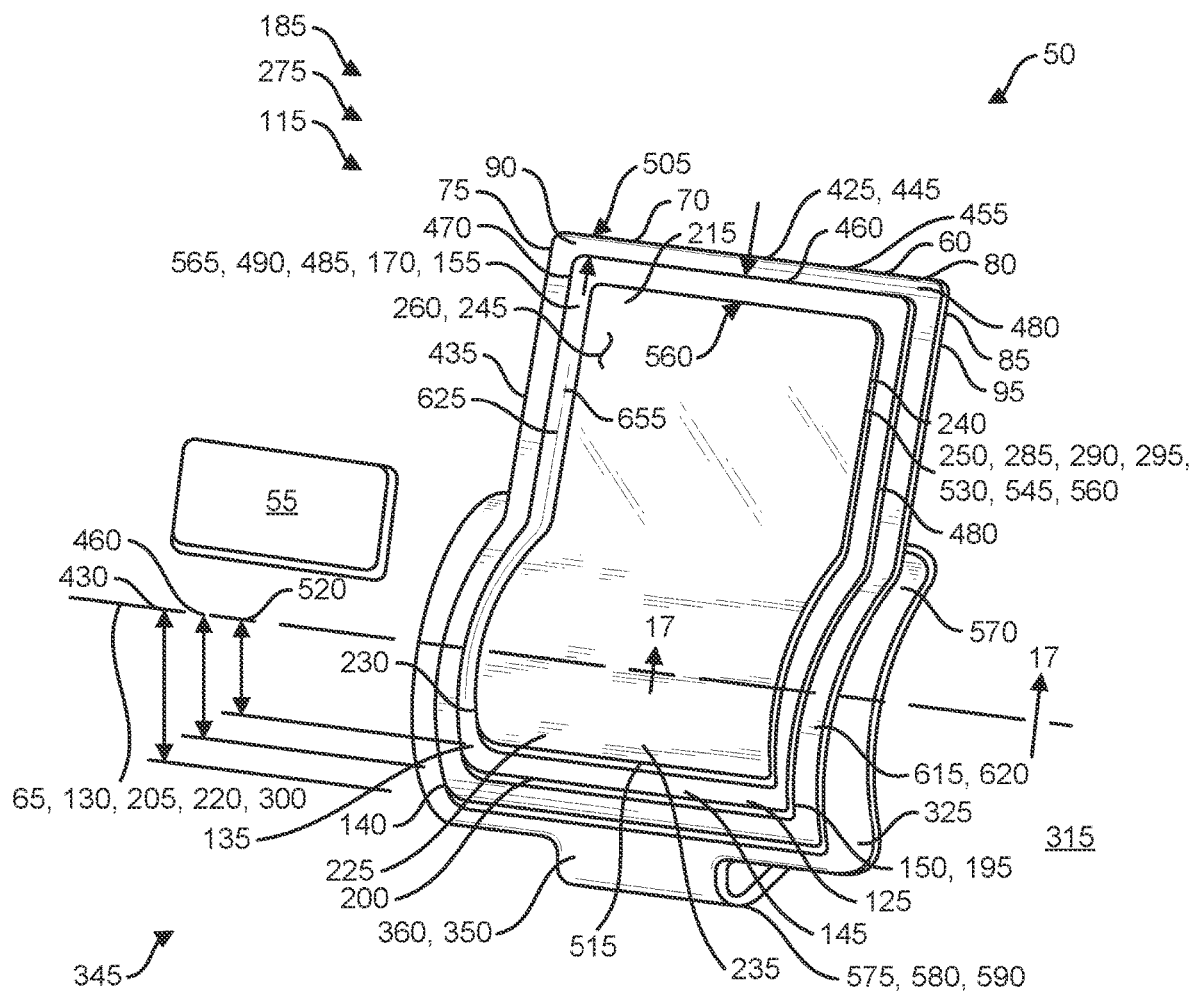
FIG. 8 shows an upper perspective view of the article shield apparatus that shows the article about to be inserted in a first, second, and third openings in their respective first, second and third alternative open states, with the strap for the second means for removable attachment that is disposed on a portion of the first outer surface.

Continuing, FIG. 8 shows an upper perspective view of the article shield apparatus 50 that shows the article 55 about to be inserted in a first 455, second 490, and third 545 openings in their respective first 435, second 470, and third 530 alternative open states, with the strap 350 for the second means 325 for removable attachment that is disposed on a portion of the first outer surface 95.

Figure 9:
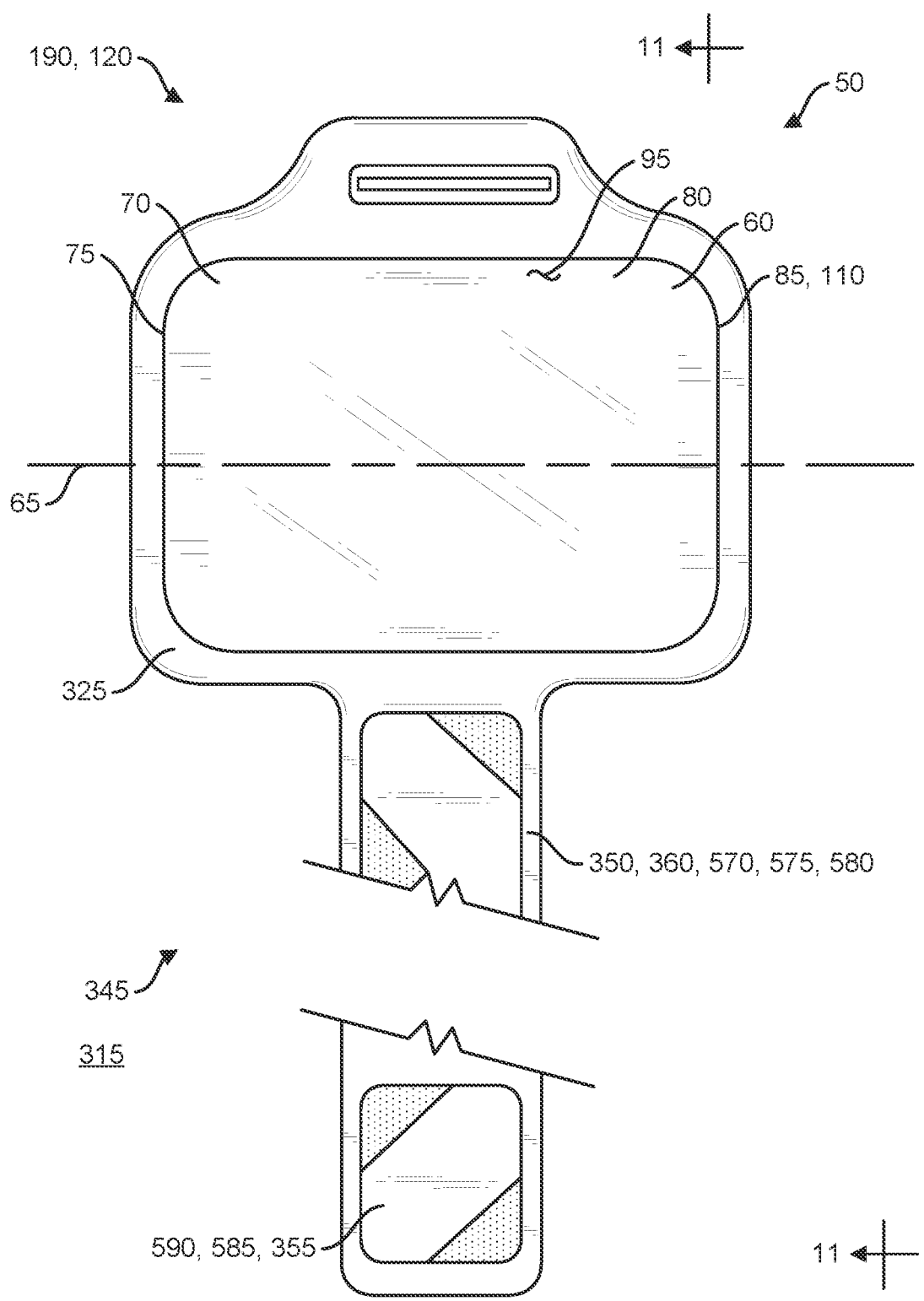
FIG. 9 shows a top flat plan view of the article shield apparatus that shows the first, second, and third aperture openings in their respective first, second and third closed states, with the strap for the second means for removable attachment that is disposed on a portion of the first outer surface.

Further, FIG. 9 shows a top flat plan view of the article shield apparatus 50 that shows the first 110, second 175, and third 265 aperture openings in their respective first 120, second 190, and third 280 closed states, with the strap 350 for the second means 325 for removable attachment that is disposed on a portion of the first outer surface 95.

Figure 10:
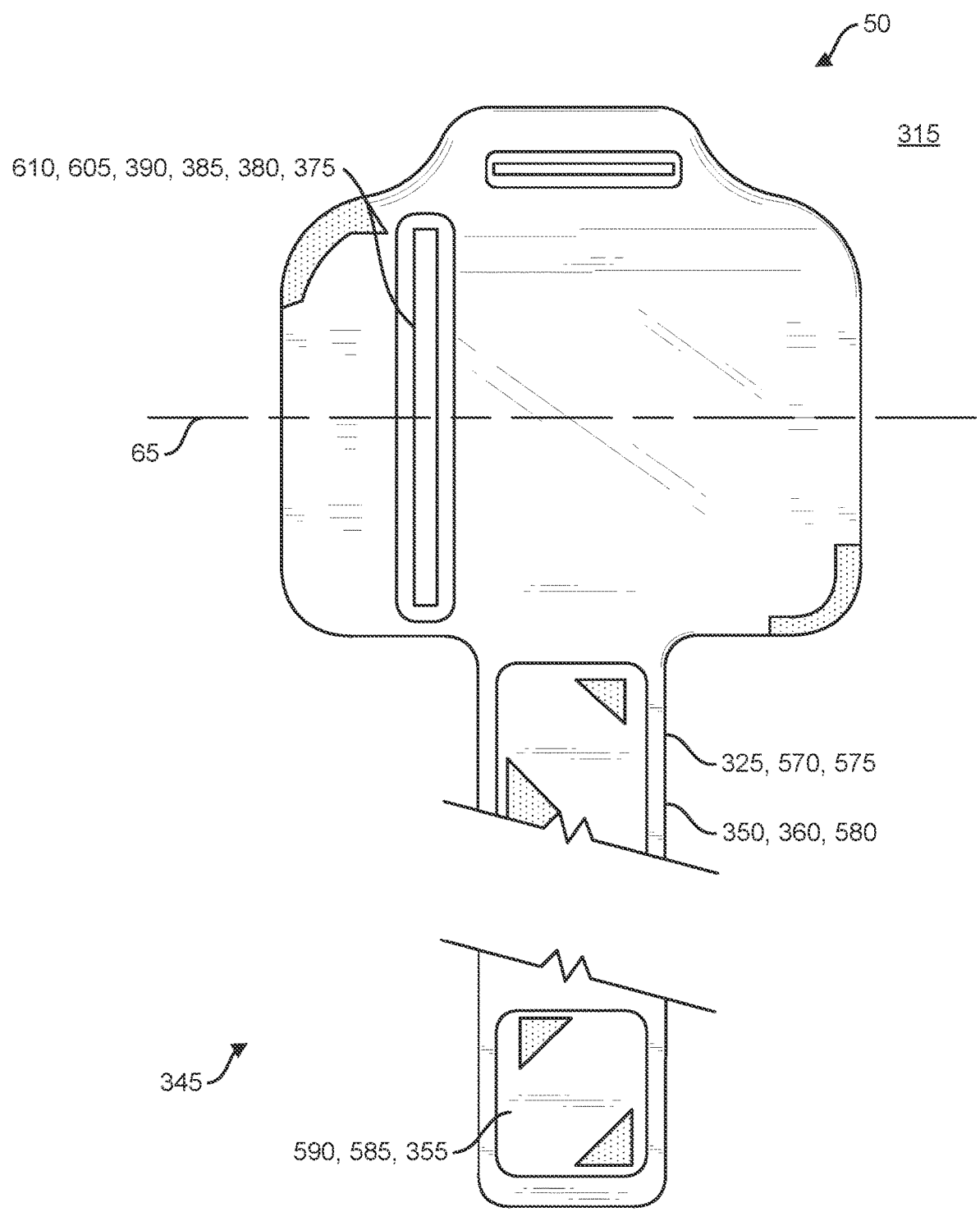
FIG. 10 shows a flat plan bottom view of the article shield apparatus that shows the pocket that is disposed between the first and second flexible surrounding sidewalls with a pocket slot.

Moving onward, FIG. 10 shows a flat plan bottom view of the article shield apparatus 50 that shows the pocket 375 that is disposed between the first 60 and second 125 flexible surrounding sidewalls with a pocket slot 380.

Figure 11:
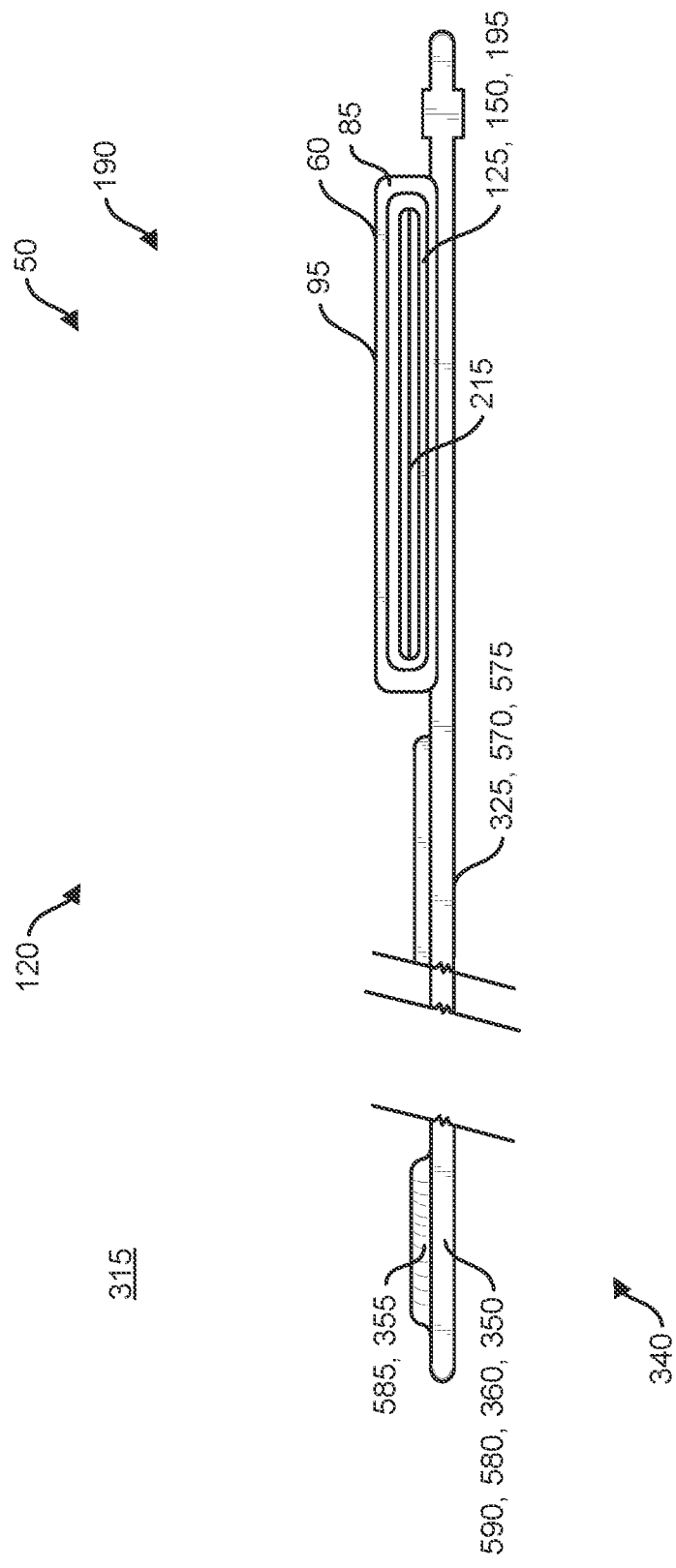
FIG. 11 shows a side elevation end view of the article shield apparatus that shows the first, second, and third flexible surrounding sidewalls in their respective first, second, and third closed states, with the strap for the second means for removable attachment that is disposed on a portion of the first outer surface.

Further, FIG. 11 shows a side elevation end view of the article shield apparatus 50 that shows the first 60, second 125, and third 215 flexible surrounding sidewalls in their respective first 120, second 190, and third 280 closed states, with the strap 350 for the second means 325 for removable attachment that is disposed on a portion of the first outer surface 95.

Figure 12:
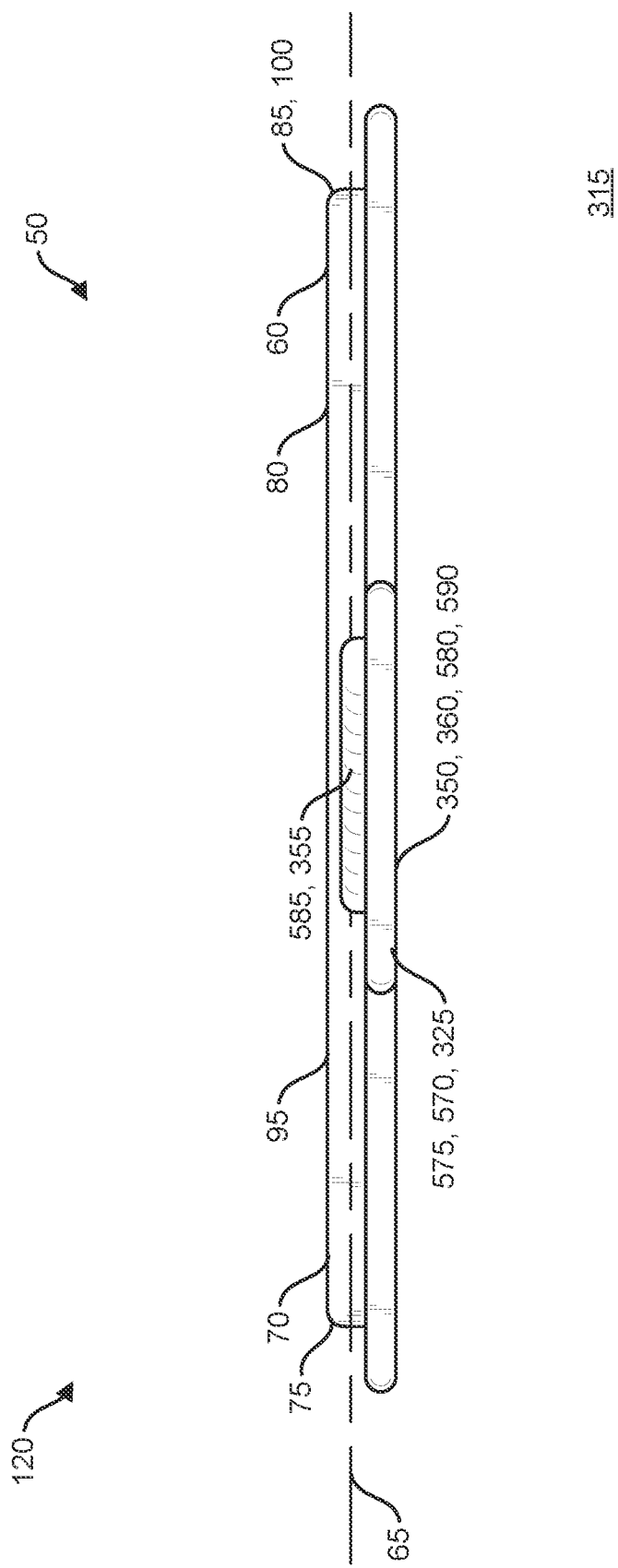
FIG. 12 shows a side elevation end view of the article shield apparatus that shows the first, second, and third flexible surrounding sidewalls in their respective first, second, and third closed states, with the strap for the second means for removable attachment that is disposed on a portion of the first outer surface.

Next, FIG. 12 shows a side elevation end view of the article shield apparatus 50 that shows the first 60, second 125, and third 215 flexible surrounding sidewalls in their respective first 120, second 190, and third 280 closed states, with the strap 350 for the second means 325 for removable attachment that is disposed on a portion of the first outer surface 95.

Figure 13:
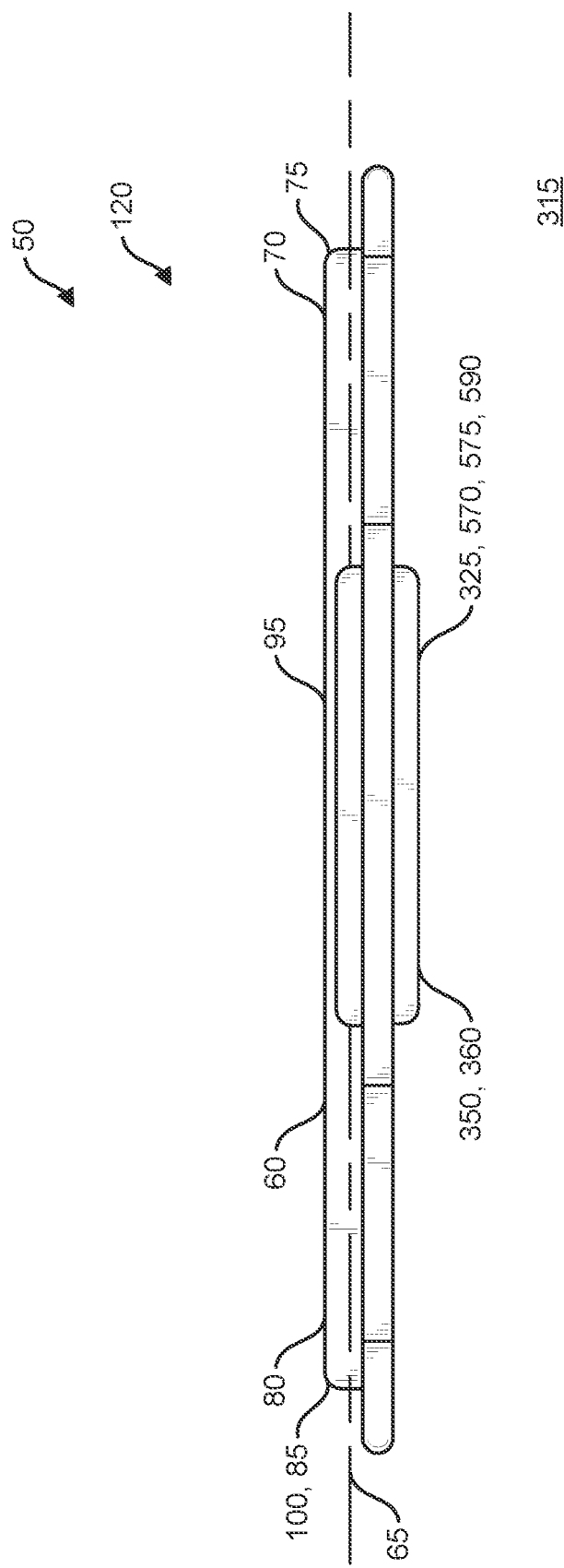
FIG. 13 shows an opposing side elevation end view of the article shield apparatus that shows the first, second, and third flexible surrounding sidewalls in their respective first, second, and third closed states, with the strap for the second means for removable attachment that is disposed on a portion of the first outer surface.

Continuing, FIG. 13 shows an opposing side elevation end view of the article shield apparatus 50 that shows the first 60, second 125, and third 215 flexible surrounding sidewalls in their respective first 120, second 190, and third 280 closed states, with the strap 350 for the second means 325 for removable attachment that is disposed on a portion of the first outer surface 95.

Figure 14:
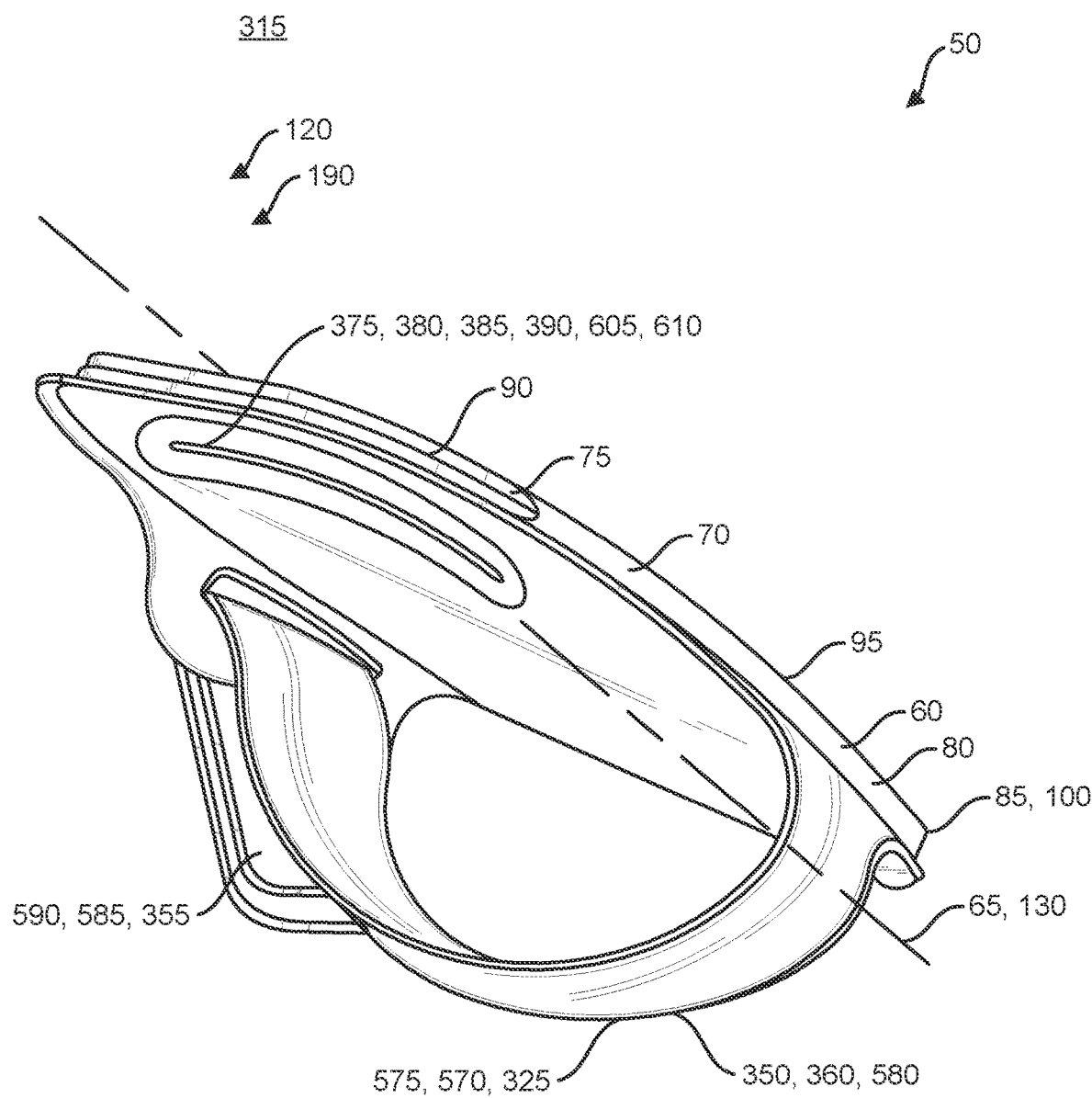
FIG. 14 shows a lower perspective view of the article shield apparatus that shows the first, second, and third flexible surrounding sidewalls in their respective first, second, and third closed states, that also shows the pocket that is disposed between the first and second flexible surrounding sidewalls with a pocket slot, further shown is the strap for the second means for removable attachment that is disposed on a portion of the first outer surface.

Further, FIG. 14 shows a lower perspective view of the article shield apparatus 50 that shows the first 60, second 125, and third 215 flexible surrounding sidewalls in their respective first 120, second 190, and third 280 closed states, that also shows the pocket 375 that is disposed between the first 60 and second 125 flexible surrounding sidewalls with the pocket slot 380, further shown is the strap 350 for the second means 325 for removable attachment that is disposed on a portion of the first outer surface 95.

Figure 15:
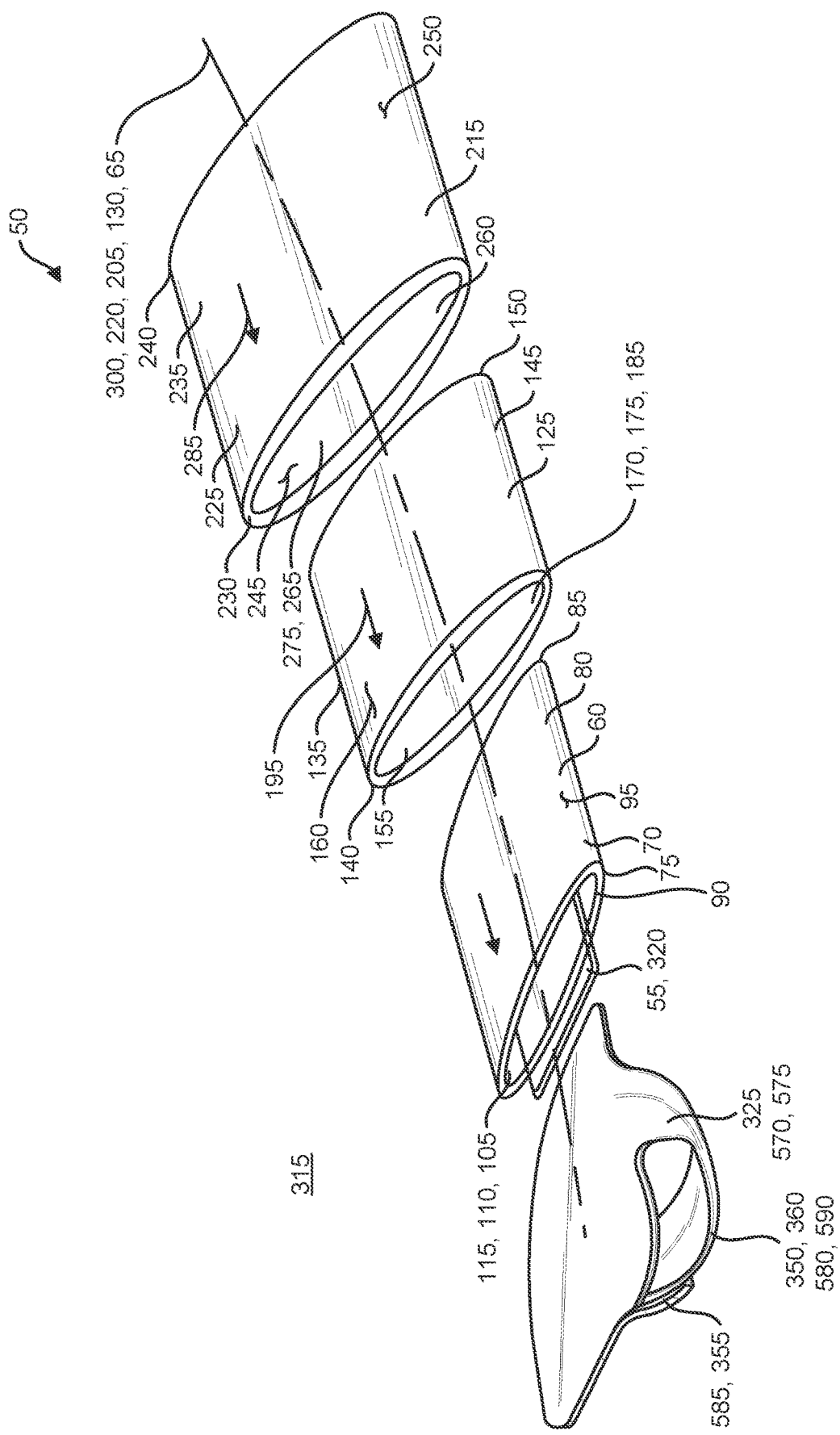
FIG. 15 shows an exploded perspective view of the article shield apparatus that shows the article that is inserted in the first, second, and third aperture openings in their respective first, second, and third open states, with the strap for the second means for removable attachment that is disposed on a portion of the first outer surface.

Moving onward, FIG. 15 shows an exploded perspective view of the article shield apparatus 50 that shows the article 55 that is inserted in the first 110, second 175, and third 265 aperture openings in their respective first 115, second 185, and third 275 open states, with the strap 350 for the second means 325 for removable attachment that is disposed on a portion of the first outer surface 95.

Figure 16:
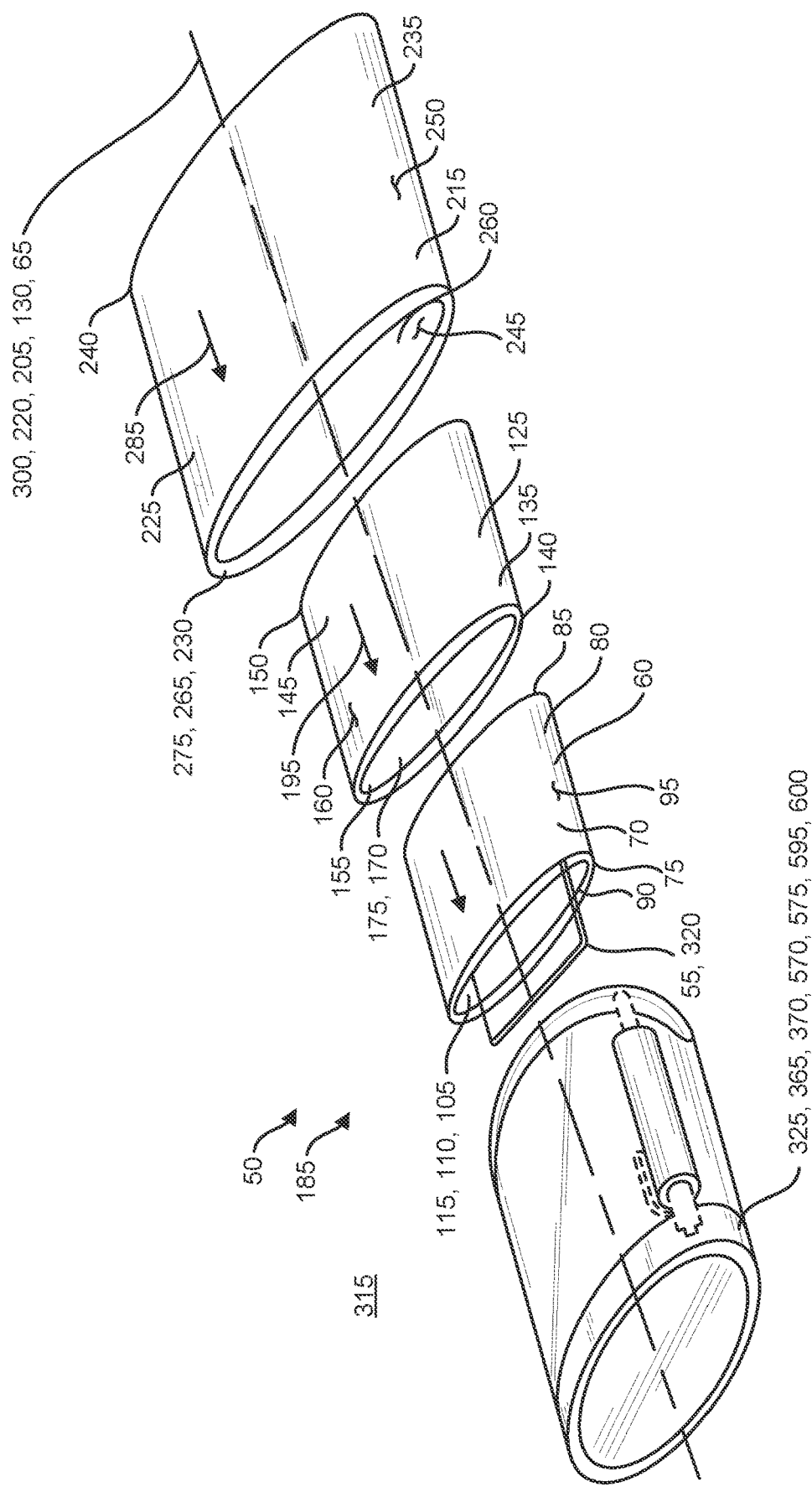
FIG. 16 shows an exploded perspective view of the article shield apparatus that shows the article that is inserted in the first, second, and third aperture openings in their respective first, second, and third open states, with the elastomeric open ended tube shape holder.

Next, FIG. 16 shows an exploded perspective view of the article shield apparatus 50 that shows the article 55 that is inserted in the first 110, second 175, and third 265 aperture openings in their respective first 115, second 185, and third 275 open states, with the elastomeric open ended tube shape holder 365.

Figure 17:
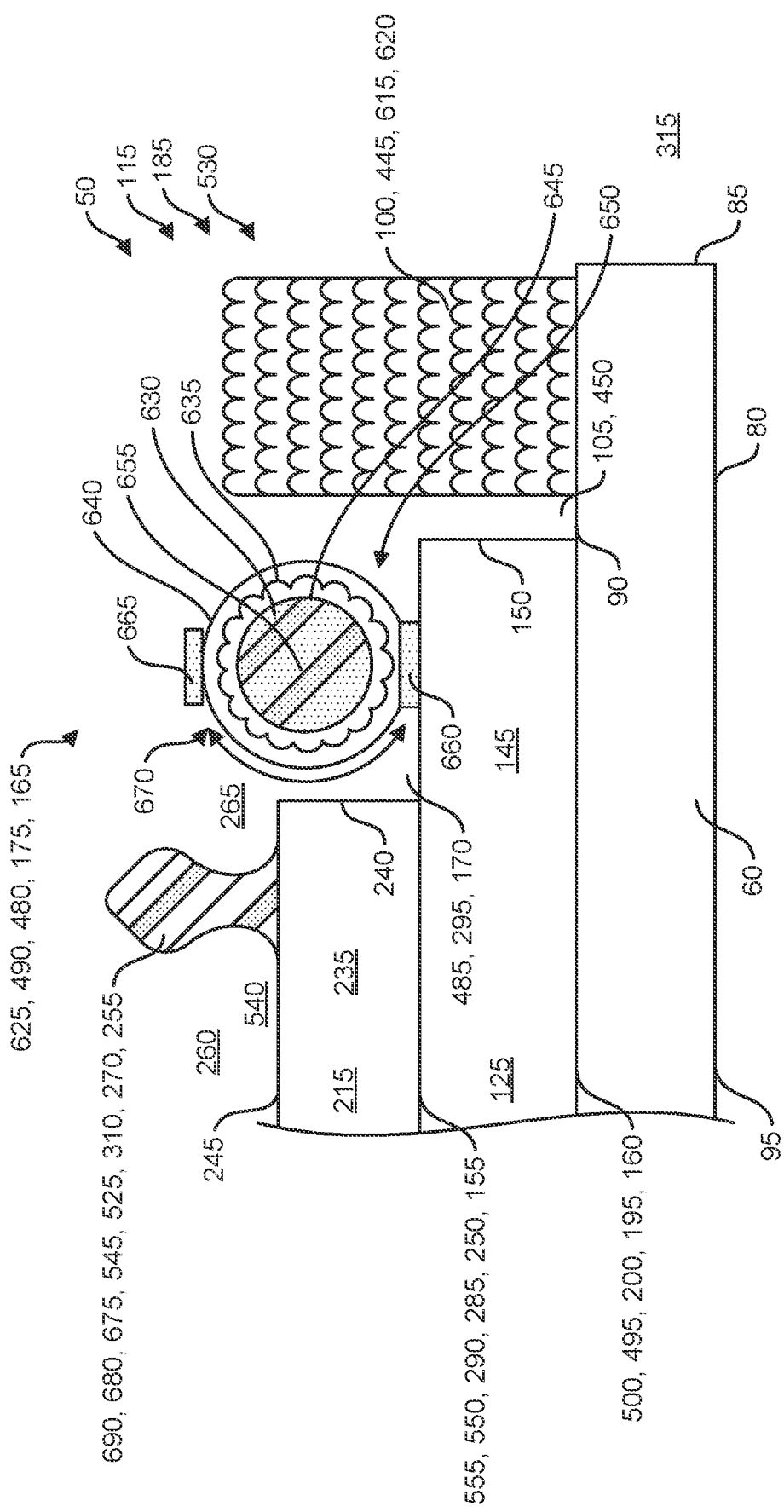

Further, FIG. 17 is cross section cut 17-17 from FIGS. 6 and 8, wherein FIG. 17 shows the first 60, second 125, and third 215 flexible surrounding sidewalls, all in the first 115, 435, second 185, 470, and third 265, 275, 530 open states, all nested 195, 285 to one another, wherein the first flexible surrounding sidewall 60 showing the fifth means 445 for removable engagement in the form of a hook and loop fastener 620, the second flexible surrounding sidewall 125 showing the sixth means 480 for removable engagement in the form of the elastically conductive flexible seal 625, and the third flexible surrounding sidewall 215 showing the first means 180 for removable engagement in the form of a waterproof seal 675 with male 680 and interlocking female 685 dovetail channels 690, again all in the first 435, second 470, and third 530 alternative open states also.

Figure 18:
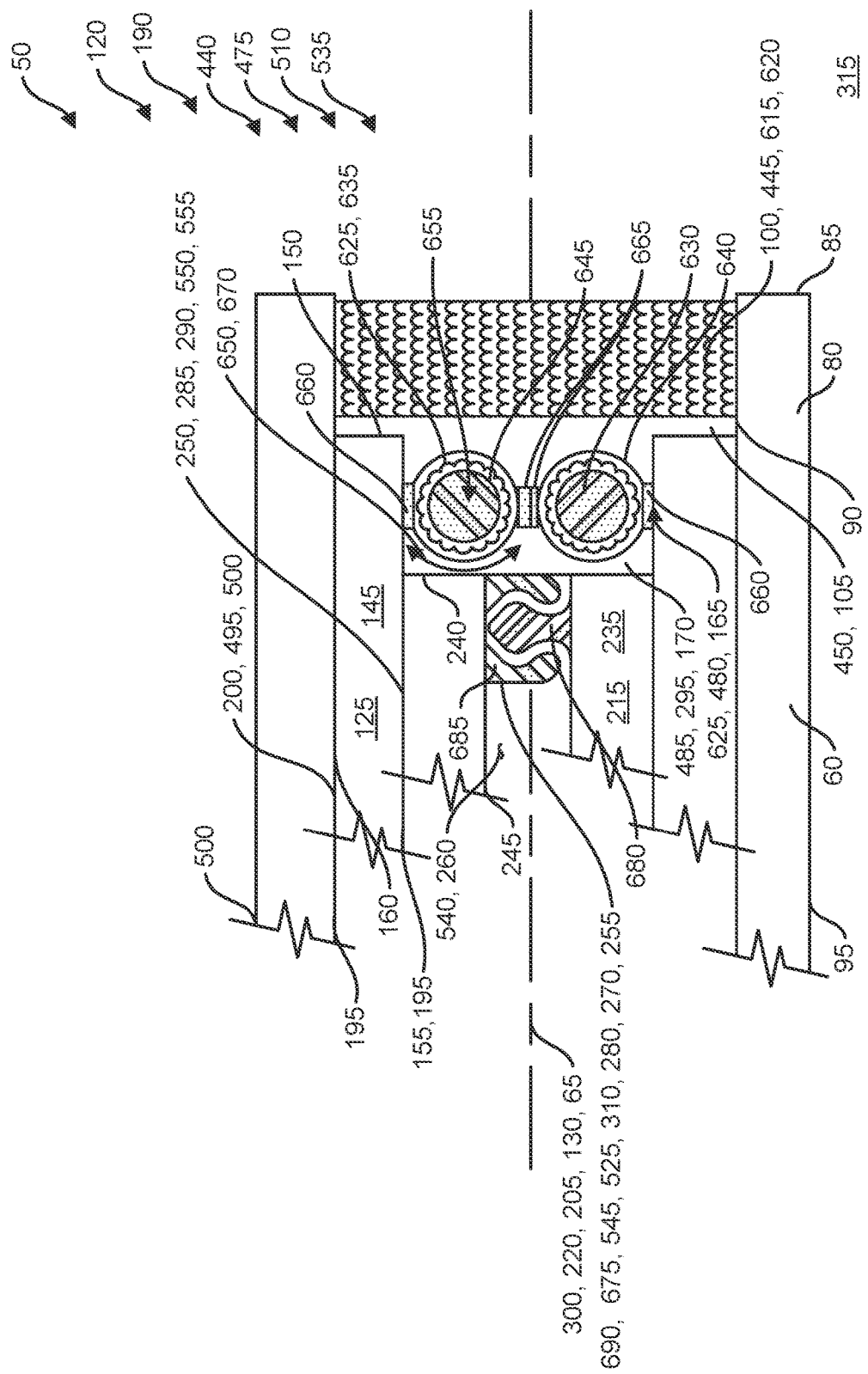

Continuing, FIG. 18 is cross section cut 18-18 from FIG. 2, wherein FIG. 18 shows the first 60, second 125, and third 215 flexible surrounding sidewalls, all in the first 120, 440, second 190, 475, and third 280, 535 closed states, all nested 195, 285 to one another, wherein the first flexible surrounding sidewall 60 showing the fifth means 445 for removable engagement in the form of a hook and loop fastener 620, the second flexible surrounding sidewall 125 showing the sixth means 480 for removable engagement in the form of the elastically conductive flexible seal 625, and the third flexible surrounding sidewall 215 showing the first means 180 for removable engagement in the form of a waterproof seal 675 with male 680 and interlocking female 685 dovetail channels 690, again all in the first 440, second 475, and third 535 alternative closed states also.

Figure 19A:
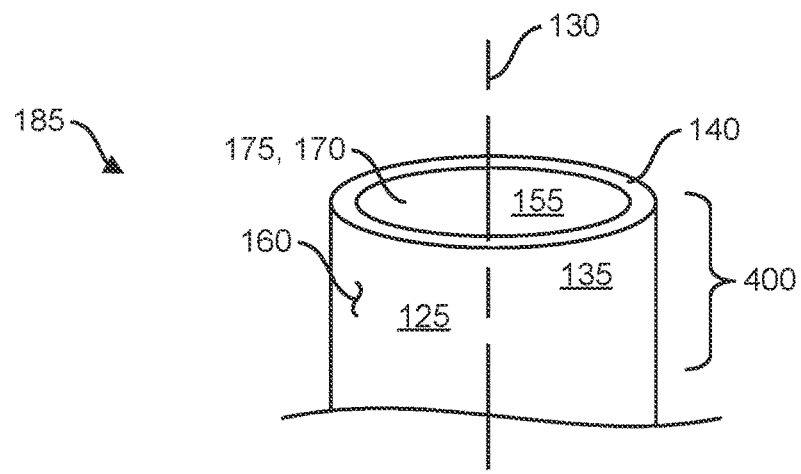
FIG. 19a is a perspective view of the second flexible surrounding sidewall with the fold over extension with the open state of the second aperture.

Next, FIG. 19a is a perspective view of the second flexible surrounding sidewall 125 with the fold over extension 400 with the open state 185 of the second aperture 175.

Figure 19B:
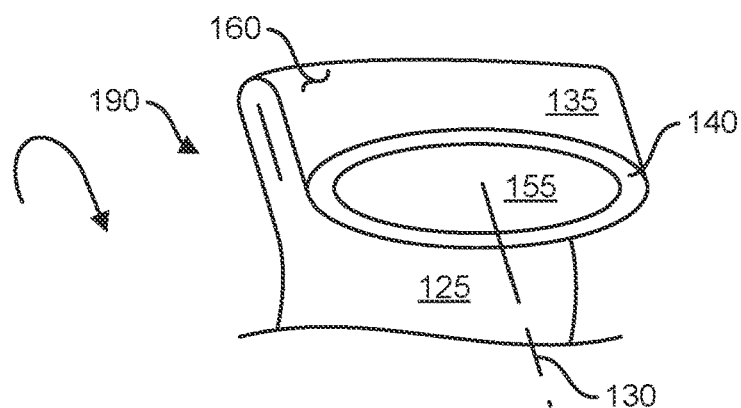
FIG. 19b is a perspective view of the second flexible surrounding sidewall with the fold over extension with the closed state of the second aperture with a first fold over.

Further, FIG. 19b is a perspective view of the second flexible surrounding sidewall 125 with the fold over extension 400 with the closed state 190 of the second aperture 175 with a first fold over.

Figure 19C:
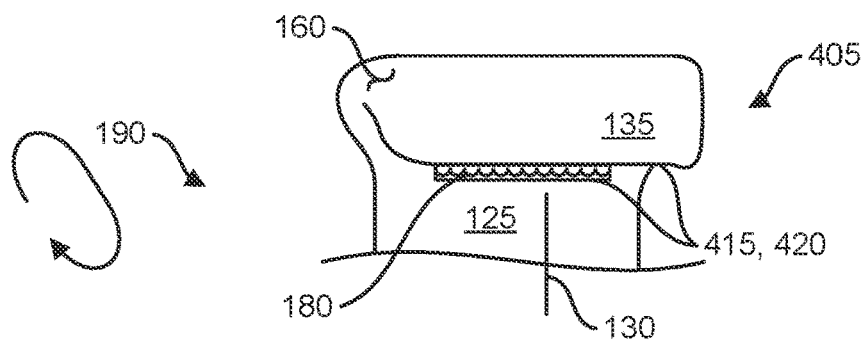
FIG. 19c is a perspective view of the second flexible surrounding sidewall with the fold over extension with the closed state of the second aperture with a second fold over utilizing the fourth means of removable engagement I the form of a hook and loop fastener.

Continuing, FIG. 19c is a perspective view of the second flexible surrounding sidewall 125 with the fold over extension 400 with the closed state 190 of the second aperture 175 with a second fold over 405 utilizing the fourth means 415 of removable engagement in the form of a hook and loop fastener 420.

Figure 19D:
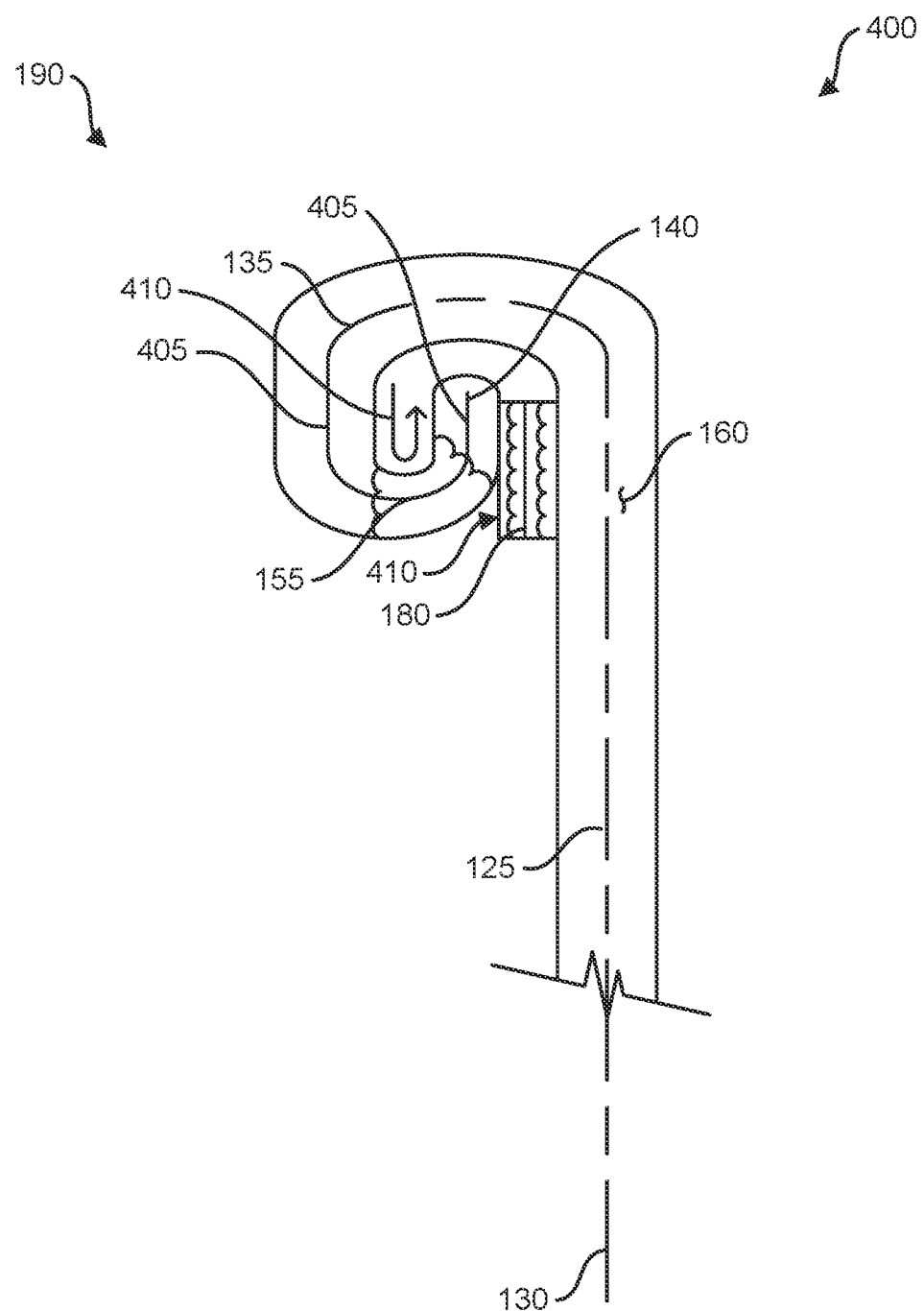

Further, FIG. 19d is a side elevation end view of the perspective view of FIG. 19c, wherein FIG. 19d shows the second flexible surrounding sidewall 125 with the fold over extension 400 with the closed state 190 of the second aperture 175 with a second fold over 405 utilizing the fourth means 415 of removable engagement the form of a hook and loop fastener 420.

Broadly, in looking at FIGS. 1 to 19a-d, the present invention is the article shield apparatus 50 adapted to protectively encompass the article 55, the article shield apparatus 50 including the first flexible surrounding sidewall 60 that is about a longitudinal axis 65, the first flexible surrounding sidewall 60 having a first primary end portion 70 terminating in a first primary margin 75 and an opposing first secondary end portion 80 terminating in a first secondary margin 85 with the longitudinal axis 65 spanning therebetween.

The first flexible surrounding sidewall 60 further including a first inner surface 90 and an opposing first outer surface 95, the first secondary margin 85 being affixed 100 to itself to form a first interior 105 as defined by the first inner surface 90 and the first primary margin 75 and said first secondary margin 85, with the first primary margin 75 defining a first aperture opening 110 that has a first open state 115 and a first closed state 120, see in particular FIGS. 1, 2, 4, 5, and FIGS. 15 to 18.

Further included in the article shield apparatus 50 is the second flexible surrounding sidewall 125 that is about a lengthwise axis 130, the second flexible surrounding sidewall 125 having a second primary end portion 135 terminating in a second primary margin 140 and an opposing second secondary end portion 145 terminating in a second secondary margin 150 with the lengthwise axis 130 spanning therebetween. The second flexible surrounding sidewall 125 further including a second inner surface 155 and an opposing second outer surface 160, the second secondary margin 150 being affixed 165 to itself to form a second interior 170 as defined by the second inner surface 155 and the second primary margin 140 and the second secondary margin 150, with the second primary margin 140 defining a second aperture opening 175.

Wherein the second primary margin 140 has a first means 180 for removable engagement, wherein the second aperture opening 175 having a second open state 185 and a second closed state 190, the second flexible surrounding sidewall 125 is nested 195 within the first interior 105 resulting in the second outer surface 160 being adjacent 200 to the first inner surface 90 and the second secondary margin 150 being adjacent to said first secondary margin 85 with the longitudinal 65 and lengthwise 130 axes being coincident 205 to one another, with the second aperture opening 175 overlaying 210 the first aperture opening 110, wherein the second flexible surrounding sidewall 125 is constructed of a radio frequency blocking material, see in particular FIGS. 6, 8, and FIGS. 15 to 18.

In addition, for the article shield apparatus 50, a third flexible surrounding sidewall 215 is included that is about a longwise axis 220, the third flexible surrounding sidewall having a third primary end portion 225 terminating in a third primary margin 230 and an opposing third secondary end portion 235 terminating in a third secondary margin 240 with the longwise axis 220 spanning therebetween. The third flexible surrounding sidewall 215 further including a third inner surface 245 and an opposing third outer surface 250, the third secondary margin 240 being affixed 255 to itself in a water proof manner to form a third interior 260 as defined by the third inner surface 245 and the third primary margin 230 and the third secondary margin 240.

With the third primary margin 230 defining a third aperture 265 opening in a third open state 275, the third flexible surrounding sidewall 215 is nested 285 within the second interior 170 resulting in the third outer surface 245 being adjacent 290 to the second inner surface 155 and the third secondary margin 240 being adjacent 295 to the second secondary margin 150 with the lengthwise 130 and longwise 220 axes being coincident 300 to one another. With the third aperture opening 265 overlaying 305 the second aperture opening 175, wherein the third flexible surrounding sidewall 215 is constructed of a waterproof material.

Wherein the third primary margin 230 further comprises a first means 270 for removable engagement in the form of a removably engageable waterproof seal 310 such that the third primary margin 230 seals unto itself to make the third interior 260 waterproof from an external environment 315 in a third closed state 280 of the third aperture opening 265. Wherein operationally, the article 55 is disposed 320 within the third interior 260 and is protected in a waterproof enclosure 215 that includes radio frequency shielding 125 with an outer cover in the form of the first flexible surrounding sidewall 60 in the first 120, second 190, and third 280 closed states, see in particular FIGS. 6, 8, and FIGS. 15 to 18.

As an option for the article shield apparatus 50, it can further comprise a second means 325 for removable attachment that is disposed on a portion of the first outer surface 95, wherein the second means 325 for removable attachment is adapted to attach 340 to a body part 330 forming a wearable 345 for the article shield apparatus 50, see FIGS. 1 to 5, 7, and FIGS. 9 to 16.

A further option for the article shield apparatus 50, is where the second means 325 is constructed of a strap 350 with a hook and loop fastener 355 that is adapted to removably engage 360 the wrist 335, see in particular FIG. 7, and FIGS. 9 to 15.

Another option for the article shield apparatus 50, is where the second means 325 is constructed of an elastomeric open ended tube shape 365 that is adapted to removably engage 370 a wrist 335, see FIGS. 1 to 5 and FIG. 16.

A following option for the article shield apparatus 50, that can further comprise a pocket 375 disposed between the first 60 and second 125 flexible surrounding sidewalls that has a pocket 375 slot 380 opening to manually 385 open and close the pocket 375 slot 380, see FIGS. 3 to 5, 10, and 14.

A continuing option for the article shield apparatus 50, wherein the pocket 375 slot 380 can further comprises a third means 390 for removable engagement, wherein the third means 390 for removable engagement is preferably constructed of a zipper 395, see FIGS. 3, 4, and 5.

Optionally, for the article shield apparatus 50, wherein the first means 180 for removable engagement is constructed of a fold over extension 400 of the second flexible surrounding sidewall 125 second primary margin 140 that has at least two-fold overs 405 to form a tortuous path 410 for helping to block radio frequency signals therethrough the second aperture opening 175, see FIGS. 19a, 19b, 19c, and 19d.

Further optionally, for the article shield apparatus 50, wherein the fold over extension 400 further comprises a fourth means 415 for removably engaging the at least two-fold overs 405, see again FIGS. 19a, 19b, 19c, and 19d. Also, the fourth means 415 is preferably constructed of a hook and loop fastener 420, see FIGS. 19a, 19b, 19c, and 19d.

The article shield apparatus 50, is adapted to protectively encompass the article 55, the article shield apparatus 50 includes the first flexible surrounding sidewall 60 that is about the longitudinal axis 65, the first flexible surrounding sidewall 60 having the first primary end portion 70 terminating in the first primary margin 75 and the opposing first secondary end portion 80 terminating in the first secondary margin 85 with the longitudinal axis 65 spanning therebetween. The first flexible surrounding sidewall 60 having the first axial margin 425 that is positioned parallel 430 to the longitudinal axis 65, the first flexible surrounding sidewall 60 further including a first inner surface 90 and the opposing first outer surface 95, the first primary margin 75, the first axial margin 425, and the first secondary margin 85 all have the fifth means 445 for removable engagement.

This is to operationally facilitate attachment in a first alternative closed state 440 and removal in a first alternative open state 435 of the first primary margin 75 to itself, the first axial margin 425 to itself, and the first secondary margin 85 to itself, further a first alternative interior 450 as defined by the first inner surface 90, the first primary margin 75, the first axial margin 425, and the first secondary margin 85 all being in the first alternative closed state 440, wherein the first opening 455 is formed for said the flexible surrounding sidewall 60 in the first alternative open state 435, see FIGS. 6, 8, 17, and 18.

Further included for the article shield apparatus 50, is the second flexible surrounding sidewall 125 that is about the lengthwise axis 130, the second flexible surrounding sidewall 125 having the second primary end portion 135 terminating in the second primary margin 140 and the opposing second secondary end portion 145 terminating in the second secondary margin 150 with the lengthwise axis 130 spanning therebetween. The second flexible surrounding sidewall 125 having a second axial margin 460 that is positioned parallel 465 to the lengthwise axis 130, the second flexible surrounding sidewall 125 further including the second inner surface 155 and the opposing second outer surface 160, the second primary margin 140, the second axial margin 460, and the second secondary margin 150 all have a sixth means 480 for removable engagement.

This is to operationally facilitate attachment in a second alternative closed state 475 and removal in a second alternative open state 470 of the second primary margin 140 to itself, the second axial margin 460 to itself, and the second secondary margin 150 to itself. Further a second alternative interior 485 as defined by the second inner surface 155, the second primary margin 150, the second axial margin 460, and the second secondary margin 150 all being in the second alternative closed state 475. Wherein a second opening 490 is formed for the second flexible surrounding sidewall 125 in the second alternative open state 470, the second flexible surrounding sidewall 125 is nested 495 within the first alternative interior 450 resulting in the second outer surface 160 being adjacent 500 to the first inner surface 90.

With the first primary margin 75 being adjacent to the second primary margin 140, the first axial margin 425 being adjacent 505 to the second axial margin 460, the second secondary margin 150 being adjacent to the first secondary margin 85, all being in the first alternative 440 and second 475 alternative closed states, with the longitudinal 65 and lengthwise 130 axes being coincident 205 to one another, . . . with the second opening 490 underlaying 510 the first opening 455, wherein the second flexible surrounding sidewall 125 is constructed of a radio frequency blocking material, see in particular FIGS. 6, 8, 17, and 18.

Further included for the article shield apparatus 50, is the third flexible surrounding sidewall 215 that is about the longwise axis 220, the third flexible surrounding sidewall 215 having the third primary end portion 225 terminating in the third primary margin 230 and the opposing third secondary end portion 235 terminating in the third secondary margin 240 with the longwise axis 220 spanning therebetween. The third flexible surrounding sidewall 215 having a third axial margin 515 that is positioned parallel 520 to the longwise axis 220, the third flexible surrounding sidewall 215 further including a third inner surface 245 and the opposing third outer surface 250, the third primary margin 230, the third axial margin 515, and the third secondary margin 240, all have a first means 270 for removable engagement in the form of a removably engageable waterproof seal 525.

This is to operationally facilitate attachment in the third alternative closed state 535 and removal in the third alternative open state 530 of the third primary margin 230 to itself, the third axial margin 515 to itself, and the third secondary margin 240 to itself. Further, the third alternative interior 540 is defined by the third inner surface 245, the third primary margin 230, the third axial margin 515, and the third secondary margin 240 all being in the third alternative closed state 535. Wherein the third opening 545 is formed for the third flexible surrounding sidewall 215 in the third alternative open state 530, the third flexible surrounding sidewall 215 is nested 550 within the second alternative interior 485 resulting in the third outer surface 250 being adjacent 555 to the second inner surface 155.

The second primary margin 140 being adjacent 560 to the third primary margin 230, the second axial margin 460 being adjacent to the third axial margin 515, the second secondary margin 150 being adjacent 295 to the third secondary margin 240, all being in the second alternative 475 and third alternative closed states 535, with the lengthwise 130 and longwise 220 axes being coincident 300 to one another, . . . with the third opening 545 underlaying 565 the second opening 490, wherein the third flexible surrounding sidewall 215 is constructed of a waterproof material. Thus making the third interior 260 waterproof from the external environment 315, wherein operationally the article 55 is disposed 320 within the third interior 260 and is protected in the waterproof enclosure that includes radio frequency shielding with the outer cover in the form of the first flexible surrounding sidewall 60 in the first alternative 440, second alternative 475, and third alternative 535 closed states, see again in particular FIGS. 6, 8, 17, and 18.

As an option for the article shield apparatus 50, it can further comprise a seventh means 570 for removable attachment that is disposed on a portion of the first outer surface 95, wherein the seventh means 570 for removable attachment is adapted 575 to attach to the body part 330 forming the wearable 345 for the article shield apparatus 50, see FIGS. 6 and 8.

Another option for the article shield apparatus 50, is where the seventh means 570 is preferably constructed of a strap 580 with a hook and loop fastener 585 that is adapted to removably engage 590 the wrist 335, see FIG. 8 and FIGS. 10 to 14.

A further option for the article shield apparatus 50, wherein the seventh means 570 is preferably constructed of an elastomeric open ended tube shape 595 that is adapted to removably engage 600 the wrist 335, see FIGS. 2 to 6 and FIG. 16.

A continuing option for the article shield apparatus 50, that can further comprise a pocket 375 disposed between the first 60 and second 125 flexible surrounding sidewalls that has a pocket 375 slot 380 opening to manually 385 open and close the pocket 375 slot 380, see FIGS. 3 to 5, 10, and 14.

Next, another option for the article shield apparatus 50, wherein the pocket 375 slot 380 further comprises a eighth means 605 for removable engagement, see FIGS. 3 to 5, 10, and 14 and the eighth means 605 for removable engagement is preferably constructed of a zipper 610, see FIGS. 3, 4, and 5.

A continuing option for the article shield apparatus 50, wherein the fifth means 615 for removable engagement is preferably constructed of a hook and loop fastener 620, see FIGS. 6, 8, 17, and 18.

A further option for the article shield apparatus 50, is wherein the sixth means 480 for removable engagement is preferably constructed of an electrically conductive flexible seal 625 that adhesively attaches to the second flexible surrounding sidewall 125. The electrically conductive flexible seal 625 is structurally made of an elastomeric core 630 that is completely encased 635 by an electrically conductive flexible fabric 635 having a conductive flexible fabric inner surface 645 and a conductive flexible fabric outer surface 640, wherein the conductive flexible fabric outer surface 640 assumes a substantially tube type shape 650 having a lengthways axis 655.

Wherein a first adhesive 660 is disposed along the lengthways axis 655 upon a portion of the conductive flexible fabric outer surface 640 and a second adhesive 665 is disposed upon a portion of the conductive flexible fabric outer surface 640, wherein the second adhesive 665 is positioned parallel and opposite 670 of the first adhesive 660 in relation to the lengthways axis 655. Further the second adhesive 665 is weaker in adhesive strength in relation to the first adhesive's 660 adhesive strength to facilitate easier opening from the second alternative closed state 475 to the second alternative open state 470, such that the electrically conductive flexible seal tube 650 stays adhered more to the second flexible surrounding sidewall 125 that to itself in the second alternative closed state 475, see in particular FIGS. 17 and 18, plus FIGS. 6 and 8.

Optionally, for the article shield apparatus 50, the removably engageable waterproof seal 310, 525 of the third flexible surrounding sidewall 215 is preferably constructed of a flexible releasable interlocking male and mating female channels 675 that assume a dovetail 690 type interlocking cross section, see FIGS. 17 and 18.

CONCLUSION

Accordingly, the present invention of an article shield apparatus has been described with some degree of particularity directed to the embodiments of the present invention. It should be appreciated, though; that the present invention is defined by the following claims construed in light of the prior art so modifications of the changes may be made to the exemplary embodiments of the present invention without departing from the inventive concepts contained therein.

The invention claimed is:

1. An article shield apparatus adapted to protectively encompass an article, said article shield apparatus comprising:
   (a) a first flexible surrounding sidewall that is about a longitudinal axis, said first flexible surrounding sidewall having a first primary end portion terminating in a first primary margin and an opposing first secondary end portion terminating in a first secondary margin with said longitudinal axis spanning therebetween, said first flexible surrounding sidewall having a first axial margin that is positioned parallel to said longitudinal axis, said first flexible surrounding sidewall further including a first inner surface and an opposing first outer surface, said first primary margin, said first axial margin, and said first secondary margin all have a fifth means for removable engagement to operationally facilitate attachment in a first alternative closed state and removal in a first alternative open state of said first primary margin to itself, said first axial margin to itself, and said first secondary margin to itself, further a first alternative interior as defined by said first inner surface, said first primary margin, said first axial margin, and said first secondary margin all being in said first alternative closed state, wherein a first opening is formed for said first flexible surrounding sidewall in said first alternative open state;
   (b) a second flexible surrounding sidewall that is about a lengthwise axis, said second flexible surrounding sidewall having a second primary end portion terminating in a second primary margin and an opposing second secondary end portion terminating in a second secondary margin with said lengthwise axis spanning therebetween, said second flexible surrounding sidewall having a second axial margin that is positioned parallel to said lengthwise axis, said second flexible surrounding sidewall further including a second inner surface and an opposing second outer surface, said second primary margin, said second axial margin, and said second secondary margin all have a sixth means for removable engagement to operationally facilitate attachment in a second alternative closed state and removal in a second alternative open state of said second primary margin to itself, said second axial margin to itself, and said second secondary margin to itself, further a second alternative interior as defined by said second inner surface, said second primary margin, said second axial margin, and said second secondary margin all being in said second alternative closed state, wherein a second opening is formed for said second flexible surrounding sidewall in said second alternative open state, said second flexible surrounding sidewall is nested within said first alternative interior resulting in said second outer surface being adjacent to said first inner surface, said first primary margin being adjacent to said second primary margin, said first axial margin being adjacent to said second axial margin, said second secondary margin being adjacent to said first secondary margin all being in said first alternative and second alternative closed states, with said longitudinal and lengthwise axes being coincident to one another, with said second opening overlaying underlaying said first opening, wherein said second flexible surrounding sidewall is constructed of a radio frequency blocking material, wherein said sixth means for removable engagement is constructed of an electrically conductive flexible seal that adhesively attaches to said second flexible surrounding sidewall and itself, said electrically conductive flexible seal is structurally made of an elastomeric core that is completely encased by an electrically conductive flexible fabric having a conductive flexible fabric inner surface and a conductive flexible fabric outer surface, wherein said conductive flexible fabric outer surface assumes a substantially tube type shape having a lengthways axis, wherein a first adhesive is disposed along said lengthways axis upon a portion of said conductive flexible fabric outer surface and a second adhesive is disposed upon a portion of said conductive flexible fabric outer surface, wherein said second adhesive is positioned parallel and opposite of said first adhesive in relation to said lengthways axis, further said second adhesive is weaker in adhesive strength in relation to said first adhesive's adhesive strength to facilitate easier opening from said second alternative closed state to said second alternative open state such that said electrically conductive flexible seal tube stays adhered more to said second flexible surrounding sidewall that to itself in said second alternative closed state; and
   (c) a third flexible surrounding sidewall that is about a longwise axis, said third flexible surrounding sidewall having a third primary end portion terminating in a third primary margin and an opposing third secondary end portion terminating in a third secondary margin with said longwise axis spanning therebetween, said third flexible surrounding sidewall having a third axial margin that is positioned parallel to said longwise axis, said third flexible surrounding sidewall further including a third inner surface and an opposing third outer surface, said third primary margin, said third axial margin, and said third secondary margin all have a removably engageable waterproof seal to operationally facilitate attachment in a third alternative closed state and removal in a third alternative open state of said third primary margin to itself, said third axial margin to itself, and said third secondary margin to itself, further a third alternative interior as defined by said third inner surface, said third primary margin, said third axial margin, and said third secondary margin all being in said third alternative closed state, wherein a third opening is formed for said third flexible surrounding sidewall in said third alternative open state, said third flexible surrounding sidewall is nested within said second alternative interior resulting in said third outer surface being adjacent to said second inner surface, said second primary margin being adjacent to said third primary margin, said second axial margin being adjacent to said third axial margin, said second secondary margin being adjacent to said third secondary margin all being in said second alternative and third alternative closed states, with said lengthwise and longwise axes being coincident to one another, with said third opening overlaying underlaying said second opening, wherein said third flexible surrounding sidewall is constructed of a waterproof material, making said third interior waterproof from an external environment, wherein operationally the article is disposed within said third interior and is protected in a waterproof enclosure that includes radio frequency shielding with an outer cover in the form of said first flexible surrounding sidewall in said first alternative, second alternative, and third alternative closed states.

2. An article shield apparatus according to claim 1 further comprising a seventh means for removable attachment that is disposed on a portion of said first outer surface, wherein said seventh means for removable attachment is adapted to attach to a body part forming a wearable for said article shield apparatus.

3. An article shield apparatus according to claim 2 wherein said seventh means is constructed of a strap with a hook and loop fastener that is adapted to removably engage a wrist.

4. An article shield apparatus according to claim 2 wherein said seventh means is constructed of an elastomeric open ended tube shape that is adapted to removably engage a wrist.

5. An article shield apparatus according to claim 1 further comprising a pocket disposed between said first and second flexible surrounding sidewalls that has a pocket slot opening to manually open and close said pocket slot.

6. An article shield apparatus according to claim 5 wherein said pocket slot further comprises a eighth means for removable engagement.

7. An article shield apparatus according to claim 6 wherein said eighth means for removable engagement is constructed of a zipper.

8. An article shield apparatus according to claim 1 wherein said fifth means for removable engagement is constructed of a hook and loop fastener.

9. An article shield apparatus according to claim 1 wherein said removably engageable waterproof seal of said third flexible surrounding sidewall is constructed of a flexible releasable interlocking male and mating female channels that assume a dovetail type interlocking cross section.

* * * * *